United States Patent
Houlihan et al.

(10) Patent No.: US 12,295,664 B2
(45) Date of Patent: *May 13, 2025

(54) SYSTEMS AND METHODS FOR VOLUMETRIC MEASUREMENT OF MAXIMAL ALLOWABLE WORKING VOLUME WITHIN A SURGICAL CORRIDOR

(71) Applicants: Dignity Health, San Francisco, CA (US); Arizona Board of Regents on Behalf of Arizona State University, Tempe, AZ (US)

(72) Inventors: Lena Mary Houlihan, Tempe, AZ (US); David Naughton, San Francisco, CA (US); Mark C. Preul, San Francisco, CA (US)

(73) Assignees: Dignity Health, San Francisco, CA (US); Arizona Board of Regents on Behalf of Arizona State University, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/525,693

(22) Filed: Nov. 30, 2023

(65) Prior Publication Data

US 2024/0099779 A1  Mar. 28, 2024

Related U.S. Application Data

(63) Continuation of application No. 18/044,037, filed as application No. PCT/US2021/049804 on Sep. 10, 2021, now Pat. No. 11,832,888.

(60) Provisional application No. 63/076,882, filed on Sep. 10, 2020.

(51) Int. Cl.
*A61B 34/10* (2016.01)
*A61B 34/00* (2016.01)

(52) U.S. Cl.
CPC .............. *A61B 34/10* (2016.02); *A61B 34/25* (2016.02); *A61B 2034/107* (2016.02); *A61B 2034/256* (2016.02)

(58) Field of Classification Search
CPC ... A61B 34/10; A61B 34/25; A61B 2034/256; A61B 2034/107
USPC ............................................. 345/427; 606/1
See application file for complete search history.

(56) References Cited

U.S. PATENT DOCUMENTS

| | | |
|---|---|---|
| 11,832,888 B2 * | 12/2023 | Houlihan ............... A61B 34/10 |
| 2006/0084867 A1 | 4/2006 | Tremblay et al. |
| 2010/0076563 A1 | 3/2010 | Otto et al. |
| 2011/0201932 A1 | 8/2011 | Duric et al. |
| 2013/0158557 A1 | 6/2013 | Komistek |
| 2015/0279088 A1 | 10/2015 | Ma et al. |
| 2015/0328004 A1 | 11/2015 | Mafhouz |
| 2017/0035517 A1 | 2/2017 | Geri et al. |
| 2020/0375670 A1 | 12/2020 | Bonny et al. |
| 2021/0326809 A1 | 10/2021 | Sutton et al. |

(Continued)

OTHER PUBLICATIONS

Patent Cooperation Treaty, International Search Report and Written Opinion, International Application No. PCT/US2021/049804, date of mailing Dec. 8, 2021, 7 pages.

*Primary Examiner* — Jin Ge
(74) *Attorney, Agent, or Firm* — Polsinelli PC

(57) ABSTRACT

Various embodiments of a system and associated method for determining a volume of surgical freedom using a plurality of three-dimensional extrema points along a surgical corridor in relation to a structure of interest are disclosed herein.

20 Claims, 27 Drawing Sheets

(56) References Cited

U.S. PATENT DOCUMENTS

2023/0185570 A1 6/2023 Kerr et al.
2023/0240751 A1* 8/2023 Houlihan ............... A61B 34/25
 345/427

* cited by examiner

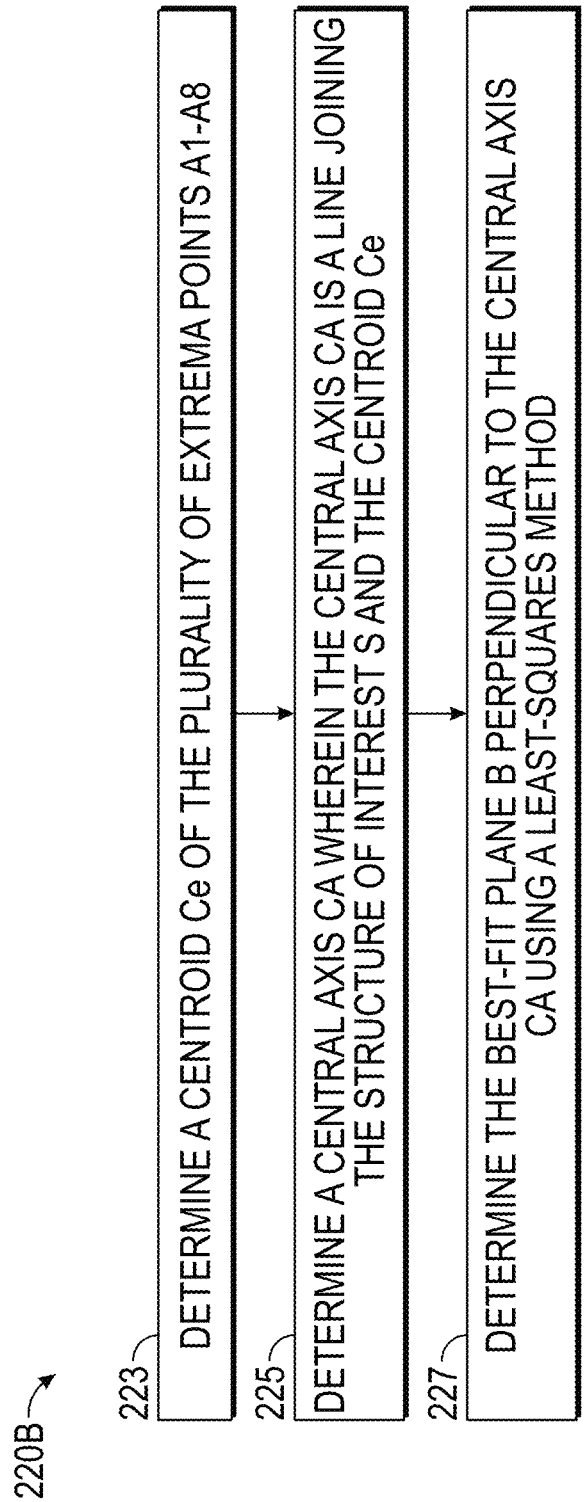

Length of Structure & Surgical Depth

Description:

Enter the X, Y and Z coordinates (in mm) of the two points. The result is the distance between the two points

|       | X      | Y      | Z      |
|-------|--------|--------|--------|
| Point 1 | 159.03 | -73.95 | 113.6  |
| Point 2 | 158.2  | -73.16 | 108.72 |

Distance 5.01272381 mm

Area of Exposure

Description:

Enter the X, Y and Z coordinates (in mm) of four points and the circumference of the area being measured. The result is the area bounded by the four points.

|   | X      | Y      | Z      |
|---|--------|--------|--------|
| 1 | 159.33 | -74.51 | 119.03 |
| 2 | 170.77 | -69    | 123.1  |
| 3 | 189.22 | -64.78 | 124.81 |
| 4 | 199.82 | -62.26 | 116.79 |

Area 1804.68894 mm²

FIG. 11A

Angle of Attack & Volume of Surgical Freedom

Description:
Enter the X, Y and Z coordinates of the apex and 8 points (in mm).
The cranio-caudal angle of attack is calculated from the angle formed by the apex and points 1 and 5.
The medio-lateral angle of attack is calculated from the angle formed by the apex and points 3 and 7.
The volume is calculated from a cone, of which the apex is the point, and the 8 points bound the area of the base of the cone.

|      | X      | Y      | Z     |
|------|--------|--------|-------|
| Apex | 131.69 | 114.14 | 99.67 |
| 1    | -25.41 | 44     | 30.12 |
| 2    | -34.65 | 54.24  | 32.9  |
| 3    | -37.52 | 54.85  | 42.34 |
| 4    | -35.39 | 41.39  | 50.88 |
| 5    | -22.11 | 17.44  | 63.16 |
| 6    | -1.09  | -7.23  | 45.49 |
| 7    | 16.9   | -21.12 | 42.41 |
| 8    | -0.44  | 2.33   | 29.38 |

Cranio-Caudal Angle: 13.176061 degrees
Medio-Lateral Angle: 29.032073 degrees

Calculate Volume of Surgical Freedom

Volume: 0 mm³
Normalized Volume: 0 mm³
Normalized Height: 10 mm

Map of 8 coordinates

| VSF Data Query-VSF Calculator × | + |
| --- | --- |
| ← → C ⟲ | ⓘ localhost:5000/query/vsfdata |

Home Home | Logout

Head Number  2
Approach  Nose Inferolateral
Manoeuver  None
Side  Left
Structure  Hcg
Laterality  None
Visualisation Method  None Get Record

FIG. 16

Home Home
Logout

Head Number: S191391
Approach: Pterional
Manoeuver: None
Side: Left
Structure: Terminal Ica
Laterality: Ipsilateral
Visualisation Method: Microscope New Head Number
New Approach
New Manoeuver
New Structure View Plot

Coordinate data

| Point | X Value | Y Value | Z Value |
|---|---|---|---|
| Apex | | | |
| 1 | 133.3 | 105.0 | 171.41 |
| 2 | 303.31 | 36.96 | 135.51 |
| 3 | 283.51 | 5.56 | 177.2 |
| 4 | 257.14 | -25.89 | 180.62 |
| 5 | 283.38 | -0.1 | 197.15 |
| 6 | 309.18 | 61.27 | 206.58 |
| 7 | 312.23 | 84.5 | 210.71 |
| 8 | 315.43 | 108.17 | 210.88 |
| Glabella | 318.19 | 59.74 | 163.93 |
| Lateral Canthus | | | |

Save Data

FIG. 20

SYSTEMS AND METHODS FOR VOLUMETRIC MEASUREMENT OF MAXIMAL ALLOWABLE WORKING VOLUME WITHIN A SURGICAL CORRIDOR

CROSS REFERENCE TO RELATED APPLICATIONS

This is a continuation application of U.S. 371 National application Ser. No. 18/044,037, filed Mar. 3, 2023, which claims benefit from International Application No. PCT/US2021/049804 filed Sep. 10, 2021, which claims benefit from U.S. Provisional Application No. 63/076,882 filed Sep. 10, 2010, all of which are herein incorporated by reference in their entireties.

FIELD

The present disclosure generally relates to quantitative anatomy, and in particular, to systems and associated methods for providing a 3-dimensional volumetric measurement of maximal allowable working volume within a surgical corridor.

BACKGROUND

Quantitative anatomy is the method by which neurosurgeons assess the surgical benefits and disadvantages of different surgical approaches using surgical technology. The purpose of studying quantitative anatomy is to improve the techniques and approaches used in neurosurgery or other related surgery disciplines. This process allows surgeons and related personnel to assess, plan and select the optimal intervention or surgical approach specific to the pathology, thereby aiming to improve surgical outcomes for patients. The ability to move and manipulate surgical instruments is an integral aspect of selecting an optimal surgical approach or comparing one surgical approach to another. This is especially relevant in neurosurgery, where surgical access through the cranium and into the deep areas of the brain is often restricted. Furthermore, in cases where the procedure is performed using an operating microscope for magnification, movement of surgical instruments to work on pathoanatomic structures may be in terms of millimetric distances. This principle of the ability to work with surgical instruments within the surgical corridor or approach is referred to as "surgical freedom." Presently, surgical freedom is defined as the maximal allowable working "area" at a proximal end of an X-mm long probe with a distal end of the probe on the target structure. However, area is not an optimal representational concept of the surgical approach corridor because area is a two-dimensional measurement, and surgical and neurosurgical approaches and corridors are volumetric, i.e., three-dimensional shapes. For instance, FIG. 2 shows a state-of-the-art representation of surgical planning as provided by a surgical neuronavigation system, which shows two-dimensional trajectory views along different anatomical planes. This description of current surgical navigational principles is the present method of planning for the surgical route and its trajectory based on a surgical neuronavigation system display. This is not a representation of surgical freedom. In addition, present approaches as aided by neuronavigation systems show the "shortest distance" or trajectory line which is not always an optimal approach. Arguably, surgical freedom is one of the most important metrics for a surgeon as it assesses the maneuverability of instruments and provides the operator insight into how realistic and appropriate using a specific surgical access corridor is. This aspect impacts the outcome of surgery for the patient.

It is with these observations in mind, among others, that various aspects of the present disclosure were conceived and developed.

BRIEF DESCRIPTION OF THE DRAWINGS

FIGS. 5A and 5B are each a respective flowchart showing a first sub-method and a second sub-method for identifying a best-fit plane according to the method of FIG. 4;

FIGS. 11A and 11B are screenshots showing one embodiment of a user interface of the system application of FIG. 10;

Figure 13:
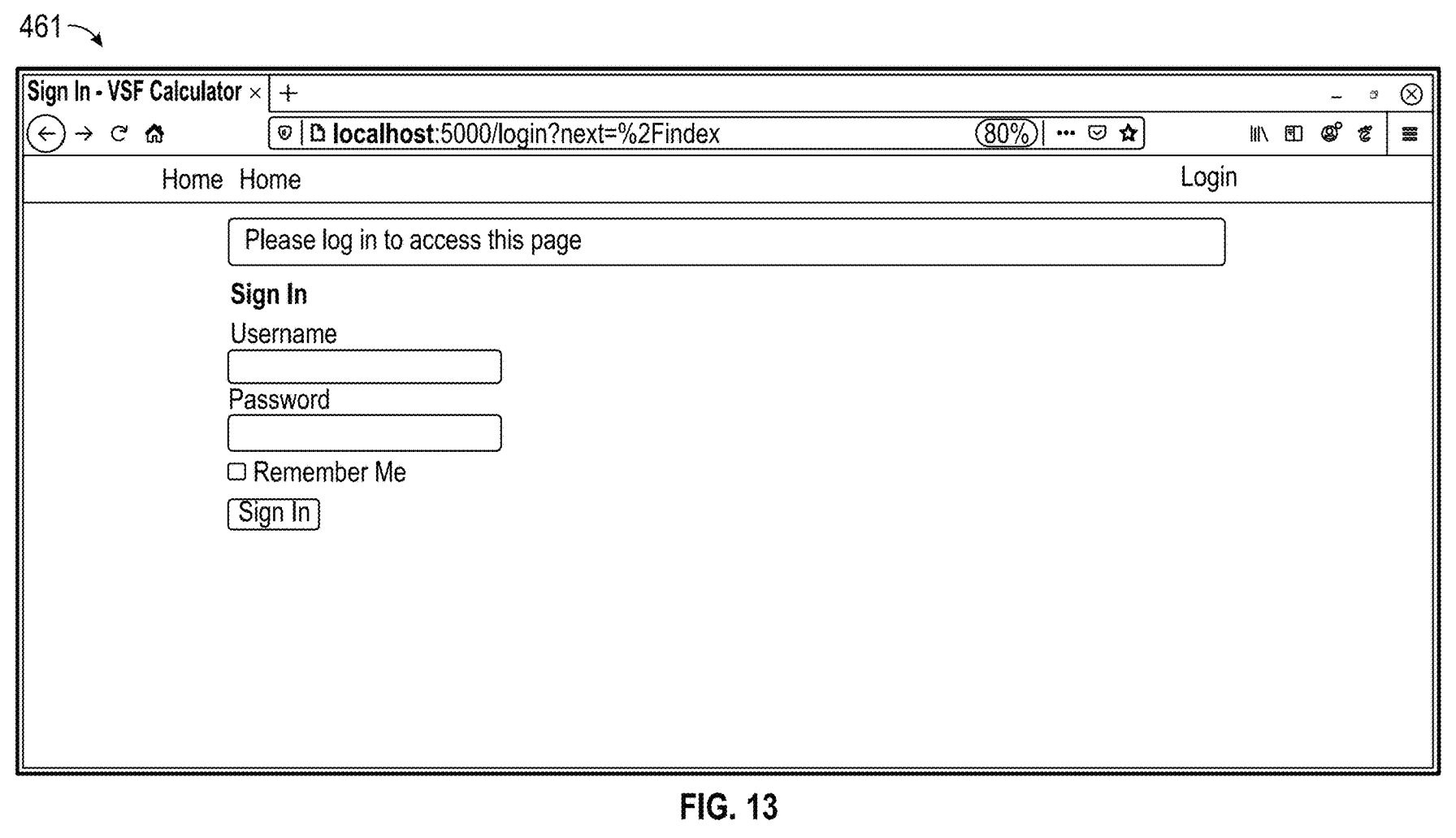

FIG. 13 is a screenshot showing a login page of the system application of FIG. 10;

FIG. 16 is a screenshot showing a search page of the system application of FIG. 10 for VSF measurements;

FIG. 20 is a screenshot showing a data entry page of the system application of FIG. 10;

DETAILED DESCRIPTION

Various embodiments of a system and associated method for determining a three-dimensional volume of surgical freedom when operating on cranial structures are disclosed herein. In one aspect, the system characterizes, assesses, and models a three-dimensional volumetric measurement of a surgical instrument's maneuverability within a surgical corridor with respect to access to a specific anatomic structure, thereby providing new insight into accessibility of an intracranial structure via a specific approach. In particular, the system and associated method provides the surgeon with a volumetric metric as to the appropriateness and utility of a surgical approach to access a specific pathology, potentially allowing neurosurgeons to plan approaches and define and provide safe access corridor guidance during planning of a surgery, including using surgical navigation, and throughout the surgery itself. Volumetric measurement of surgical freedom is a quantifiable metric for assessing the likelihood of anatomic structure injury and surgical risk.

In some embodiments, the method of determining a volume of surgical freedom is integrated into pre-operative and intra-operative planning, as well as into surgical neuronavigation software and systems. In one aspect, three-dimensional coordinates associated with a structure of interest and a plurality of extrema points around or along a surgical corridor are acquired using a neuronavigation system. The coordinates associated with the structure of interest and the plurality of extrema points are used to represent a volume of surgical freedom for an instrument to operate within a particular surgical corridor. In one method, the plurality of extrema points are used to identify a best-fit plane which serves as the base of a cone, the cone being a geometric representation of a surgical corridor in which a surgical instrument can reach a surgical structure of interest. The base of the cone represents the surgical approach or corridor access point, and the apex of the cone represents the structure of interest or target structure. The extrema points are translated to the best-fit plane and used to determine the volume of surgical freedom of an instrument relative to the surgical structure of interest.

Figure 1:
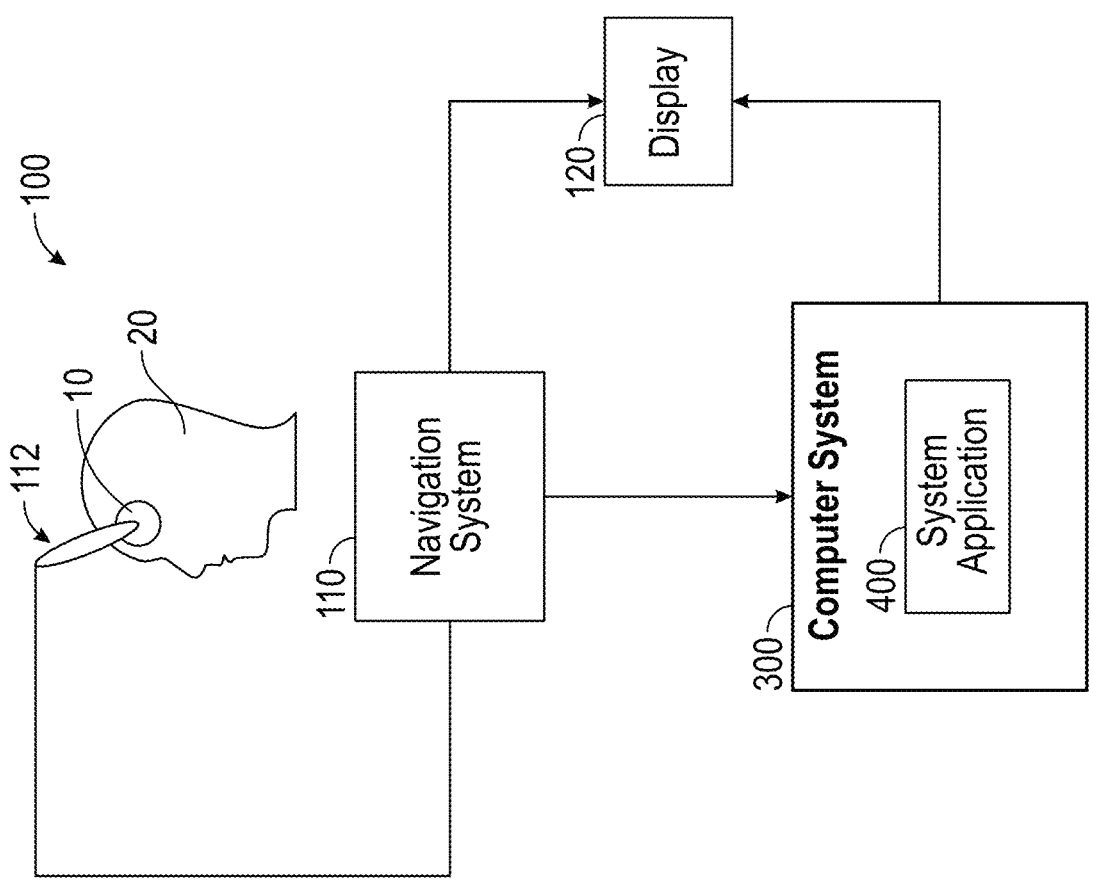
FIG. 1 is a simplified block diagram showing a system for determining a volume of surgical freedom for a procedure.
Figure 2:
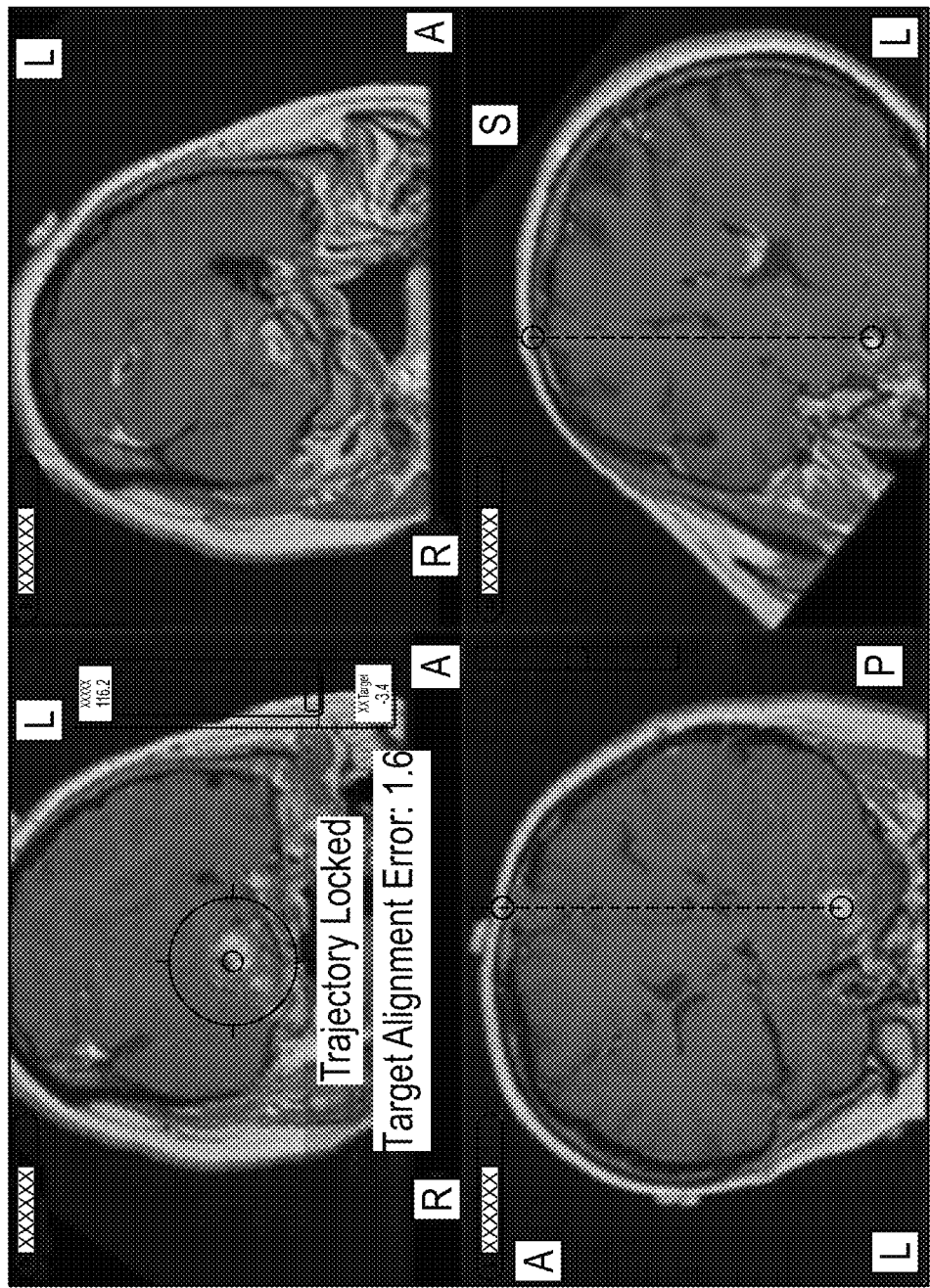
FIG. 2 is an image showing a prior art representation of current surgical trajectory planning.

Referring to FIG. 1, the system 100 includes a probe 112 in electrical communication with a navigation system 110 for identifying three-dimensional (3D) coordinates of various points along a surgical corridor 10 within a body 20. The navigation system 110 includes or is otherwise in electrical communication with a computing system 300 storing instructions for execution of a method 200 for determining a volume of surgical freedom of a surgical instrument within the surgical corridor 10. As shown, the navigation system 110 and computing system 300 are in electrical communication with a display 120, the display 120 being operable to display metrics related to a volume of surgical freedom, and in some embodiments, a three-dimensional (3-D) rendering of the surgical corridor, as determined by the computing system 300 using the method 200. In some embodiments, the system 100 and/or associated method 200 are operable to be integrated into pre-operative and intra-operative planning systems, as well as surgical neuro-navigation software and systems. One example computer-implemented application 400 for implementation of the system 100 is shown in FIGS. 10-22.

Figure 3A:
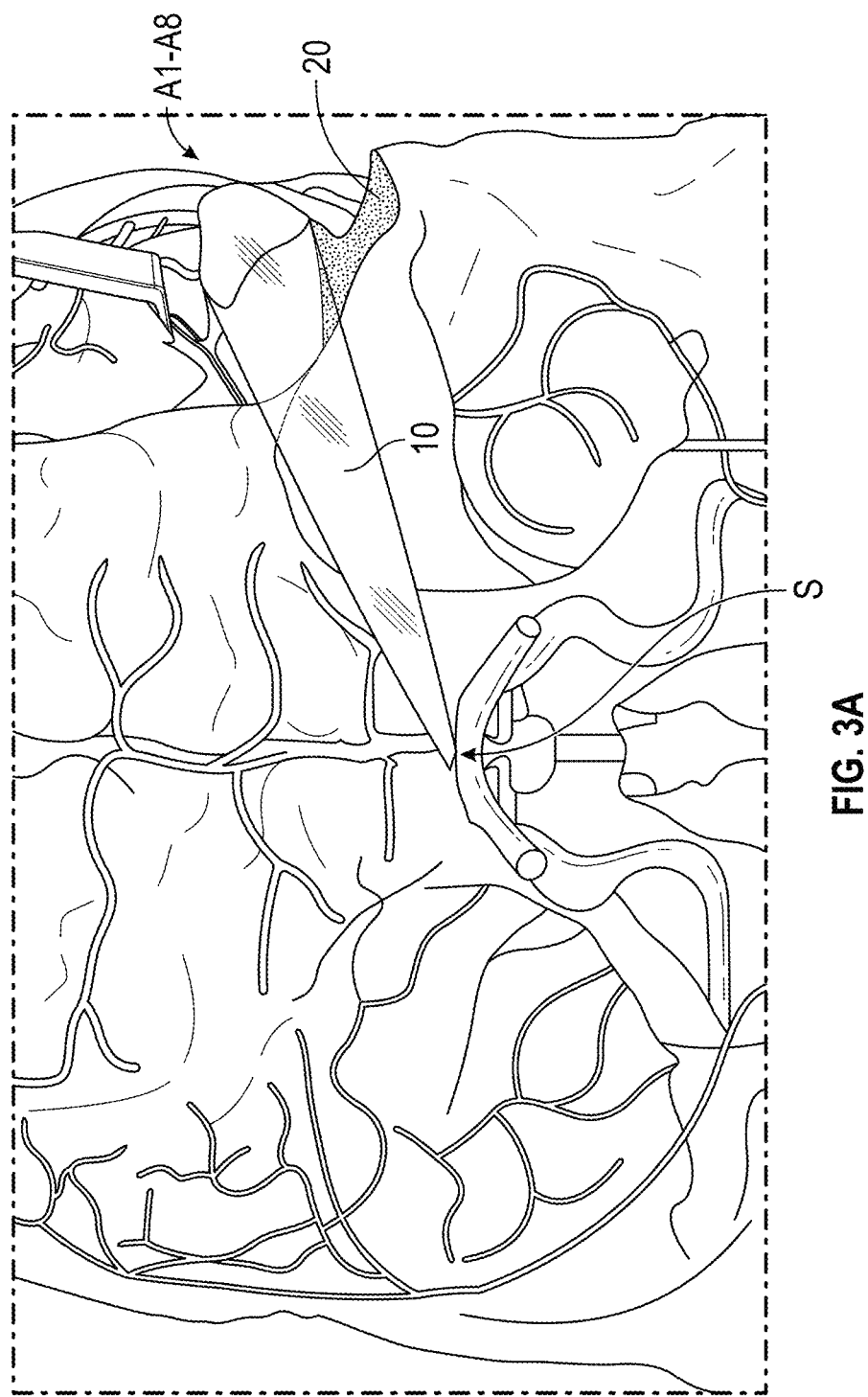
FIGS. 3A and 3B are illustrations showing a surgical corridor as identified using the system of FIG. 1 including a plurality of extrema points.
Figure 3B:
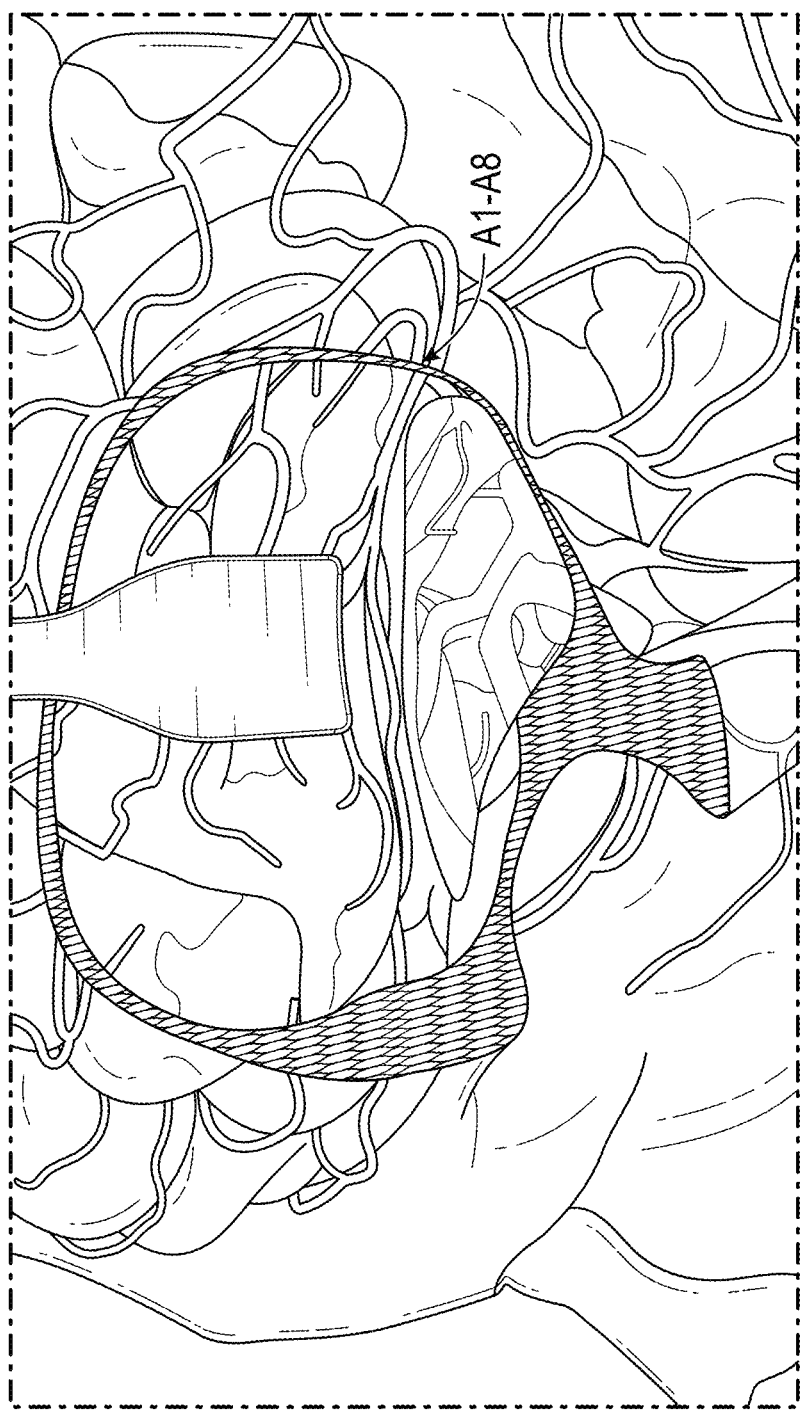

Referring to FIGS. 3A and 3B, the system 100 determines the volume of surgical freedom in relation to a measured location of a structure of surgical interest S and a measured location of a plurality of extrema points A1-A8 which are indicative of extrema of maneuverability of the probe 112 with a distal end of the probe 112 fixed to the structure of interest S. The volume of surgical freedom is a 3-D volumetric measurement of a surgical instrument's maneuverability within a surgical corridor 10 with respect to access to the specific anatomic structure of interest S. In some embodiments, the probe 112 is operable to obtain coordinate data representative of the measured locations of the structure of surgical interest S and the plurality of extrema points A1-A8.

In some embodiments, the measured location of the structure of surgical interest S and the measured locations of each extrema point A1-A8 of the plurality of extrema points A1-A8 are identified within the surgical corridor using the navigation system 110, which provides three-dimensional coordinates for the structure of interest S and each extrema point A1-A8. In some embodiments, a head of the body 20 is fixed in position while the measurements are being taken.

Figure 6:
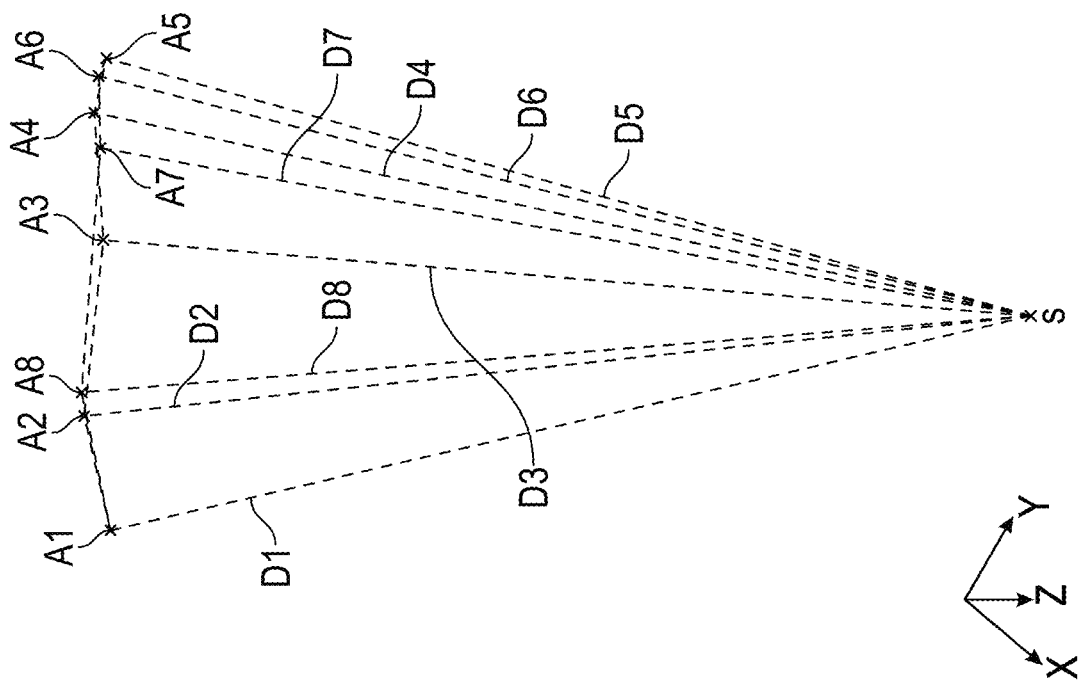
FIG. 6 is an illustration showing a plurality of extrema points in relation to a structure of interest for determining a volume of surgical freedom with respect to the structure of interest according to the method of FIG. 4.
Figure 7:
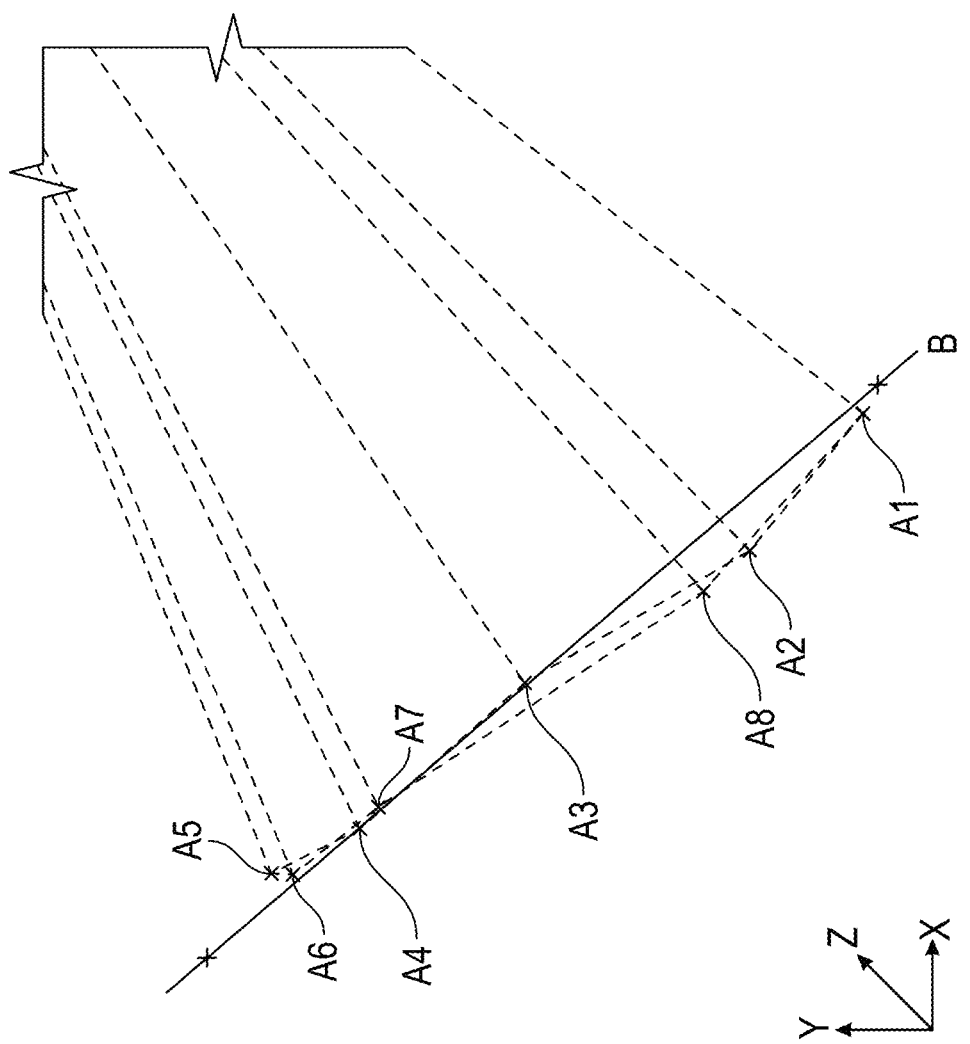
FIG. 7 is an illustration showing a best-fit plane in relation to the plurality of extrema points of FIG. 6 according to the method of FIG. 4.
Figure 8A:
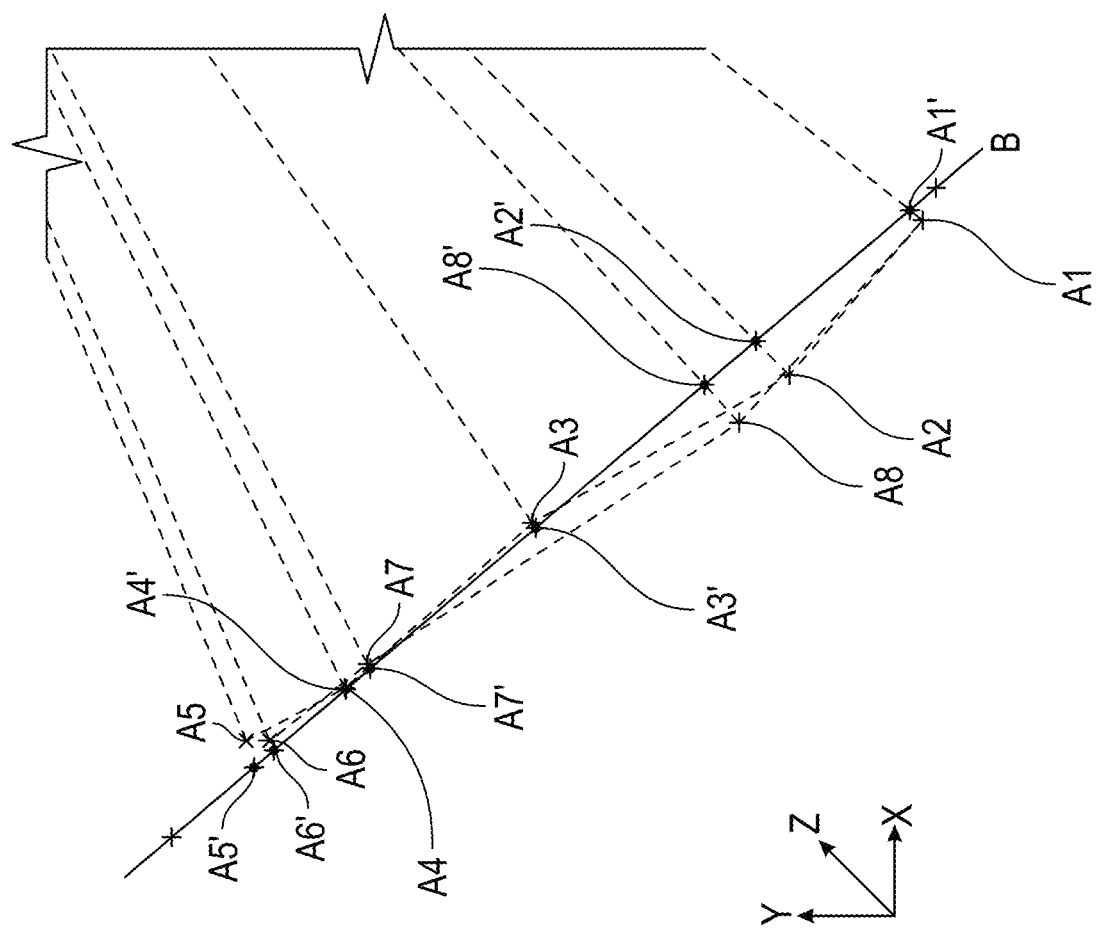
FIGS. 8A and 8B are illustrations showing a translation of each of the plurality of extrema points onto the best-fit plane of FIG. 7 according to the method of FIG. 4.
Figure 8B:
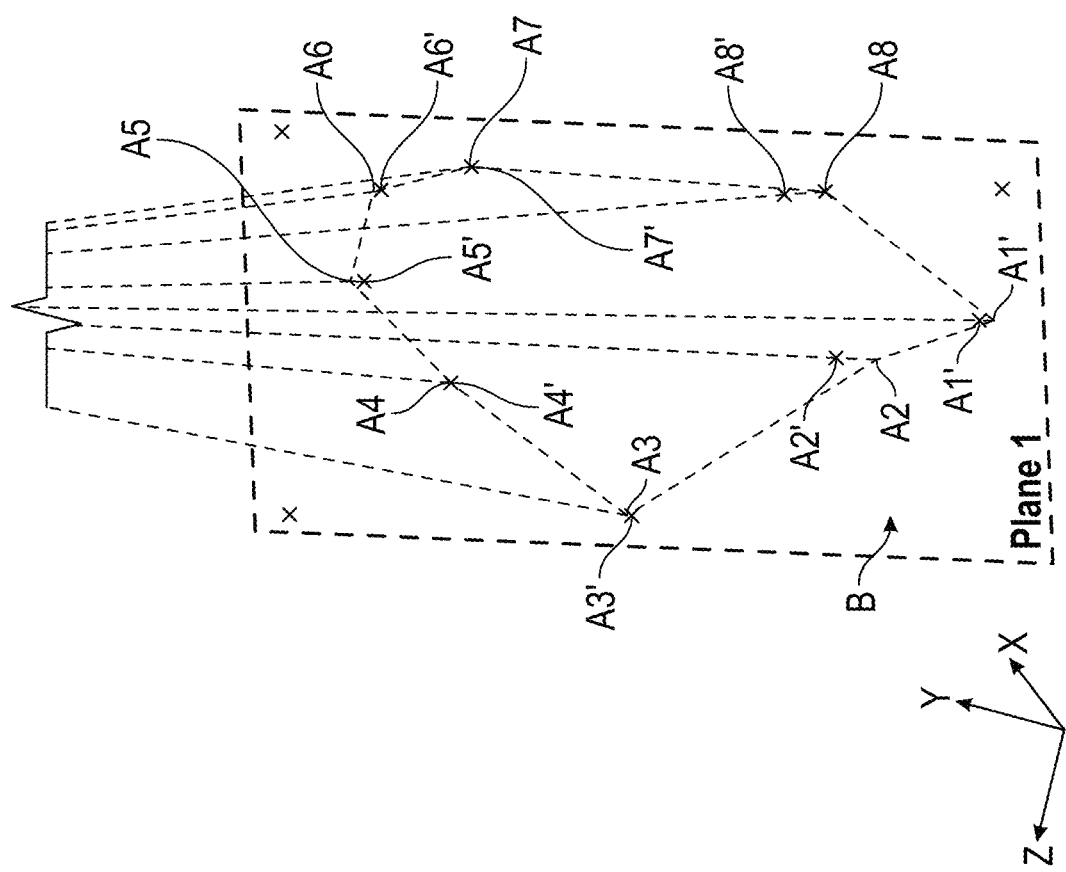
Figure 9:
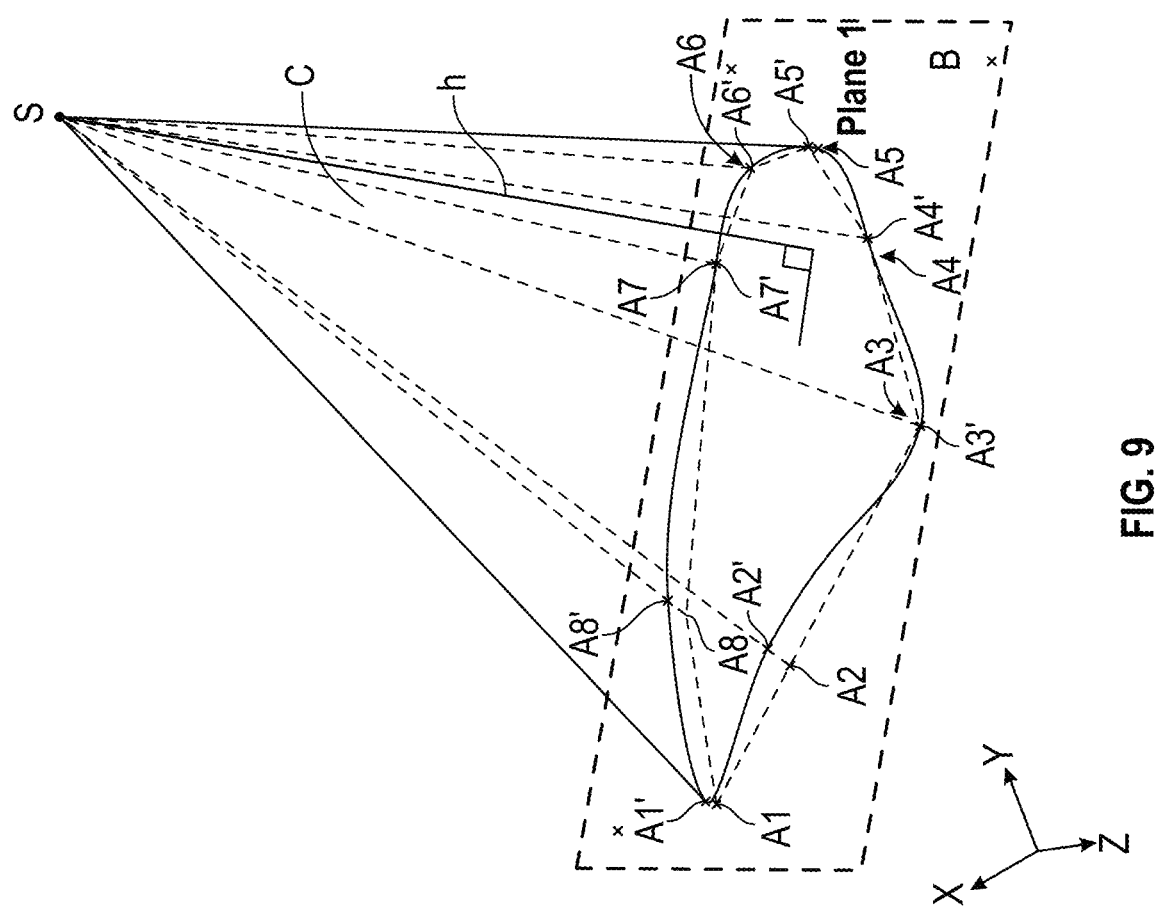
FIG. 9 is an illustration showing a cone C formed using the plurality of extrema points and the best-fit plane of FIGS. 8A and 8B including a height determined perpendicular to the best-fit plane and intersecting with the structure of interest.
Figure 10:
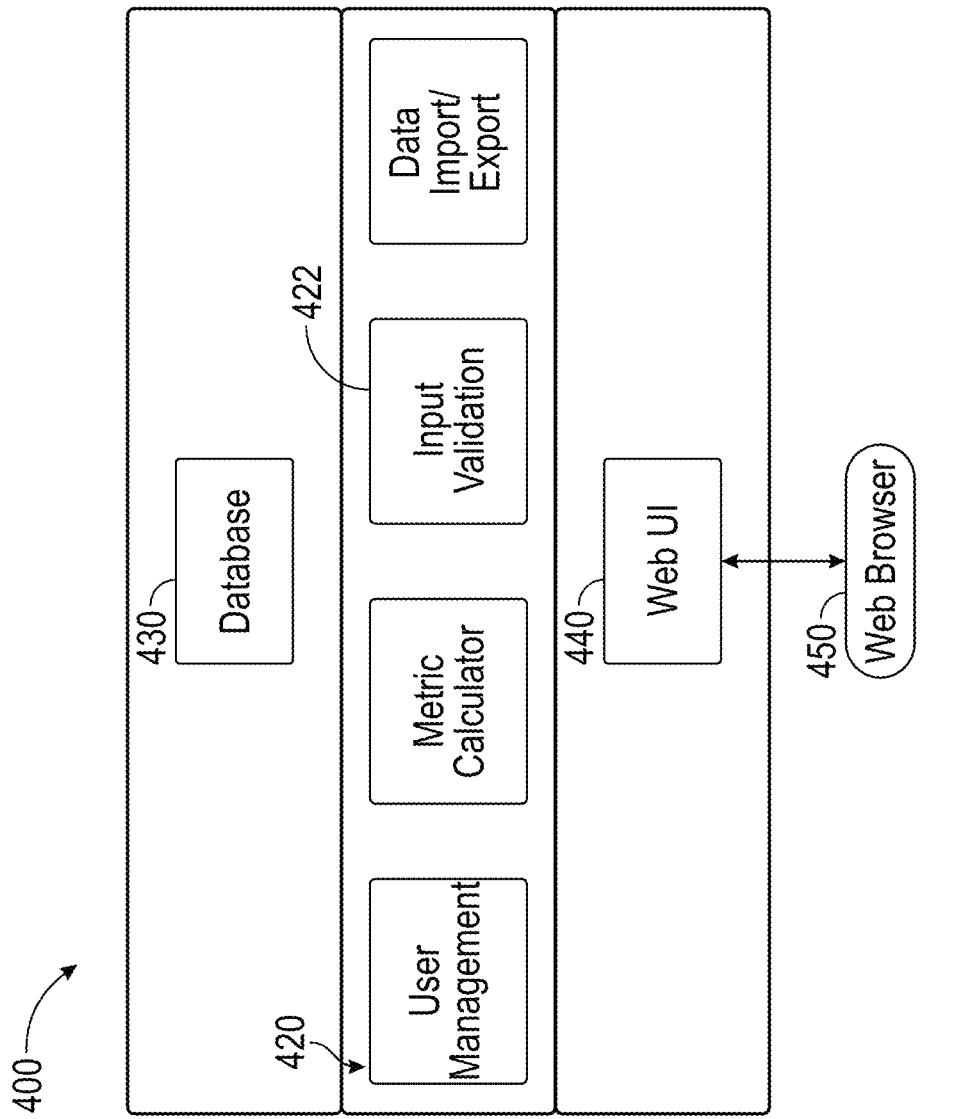
FIG. 10 is a simplified block diagram showing a system application for the system of FIG. 1.

Referring to FIGS. 4 and 6-9, a method 200 of determining a volume of surgical freedom within a surgical corridor 10 of the body 20 is illustrated. In one aspect, referring to step 210 of the method 200, the system 100 takes 3-D coordinates of a structure of interest S along with 3-D coordinates of each extrema point A1-A8 of the plurality of extrema points A1-A8 measured at various points along an extrema of maneuverability the probe 112 within a surgical corridor 10, as shown in FIG. 6. In some embodiments, the volume of surgical freedom can be visualized as a cone having an irregular base, an apex of the cone being representative of a location in 3-D space of the structure of interest S and the irregular base being representative of a plane in 3-D space, the plane being fit to the plurality of extrema points A1-A8. In step 220 of method 200, the system 100 identifies a best-fit plane B (FIG. 7) using the plurality of extrema points A1-A8 and the best-fit plane B is taken as the base of the cone C (FIG. 9). In step 230, the system 100 translates the plurality of extrema points A1-A8 onto the best-fit plane B to obtain a plurality of 3-D translated extrema points A1'-A8' (FIGS. 8A and 8B). In step 240 of method 200, the system 100 converts the 3-D coordinates of each 3-D translated extrema point A1'-A8' of the plurality of 3-D translated extrema points A1'-A8' from the 3-D coordinate system to a 2-D coordinate system on the best-fit plane B to obtain a plurality of 2-D translated points A1"-A8". In step 250 of method 200, the system 100 determines an area of an irregular polygon P enclosed by the plurality of 2-D translated points A1"-A8". In step 260 of method 200, a the system 100 determines a height value h from the best fit plane B to the structure of interest S, the height being representative of a length of a line drawn perpendicular to the best fit plane B and intersecting with the location of the structure of interest S, as shown in FIG. 9. In step 270 of the method 200, the system 100 determines a volume of surgical freedom V using the area of the irregular polygon P and the height value h.

In some embodiments of the method 200, between steps 220 and 230, the system 100 translates the best-fit plane B in 3-D space to a fixed perpendicular distance from the structure of interest S while maintaining a slope of the best-fit plane B. The inclusion of this step enables the determination of a volume of surgical freedom at a fixed distance from the structure of interest.

Figure 4:
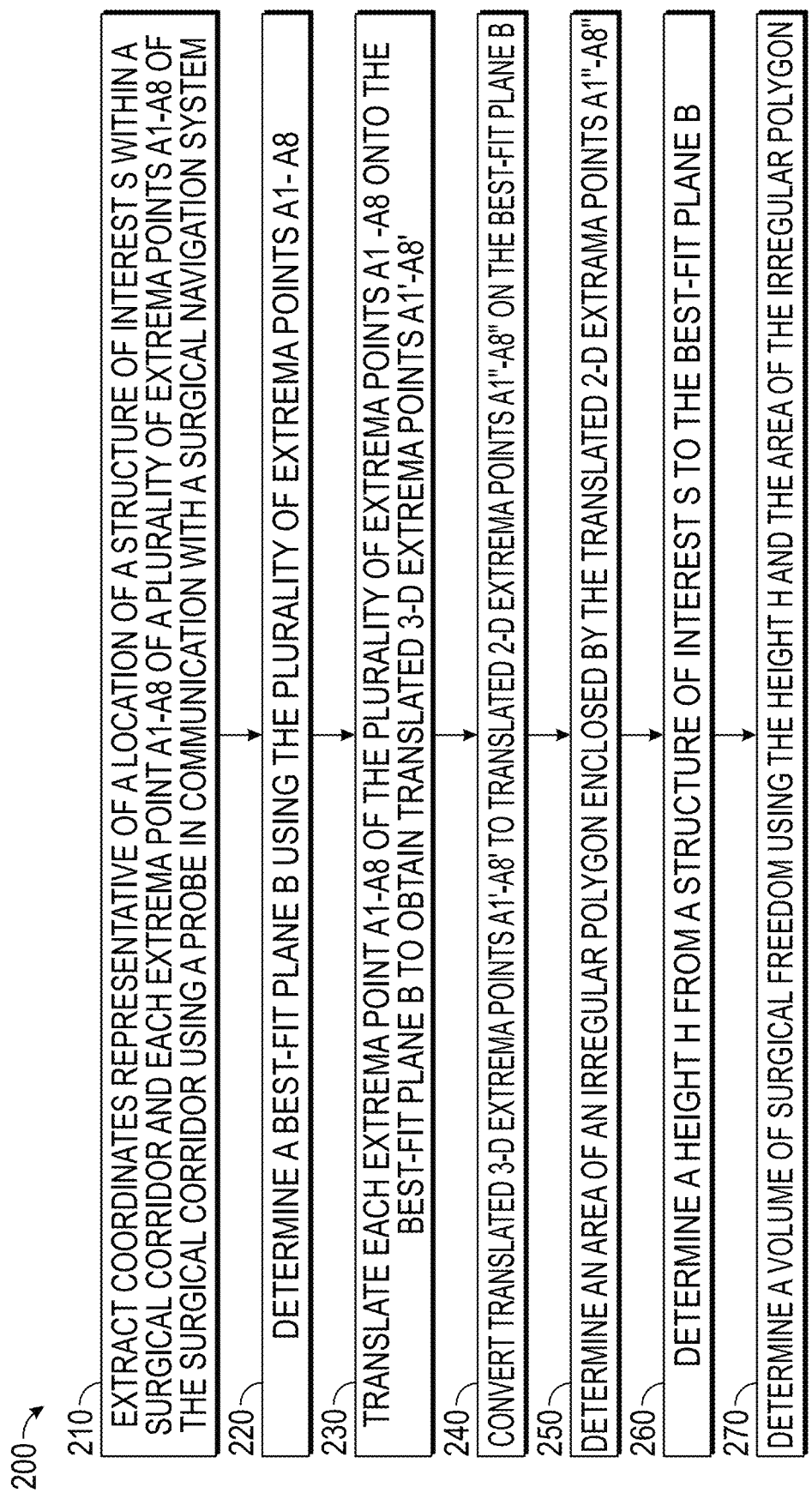
FIG. 4 is a flowchart showing a method for determining a volume of surgical freedom as executed by the system of FIG. 1.
Figure 5A:
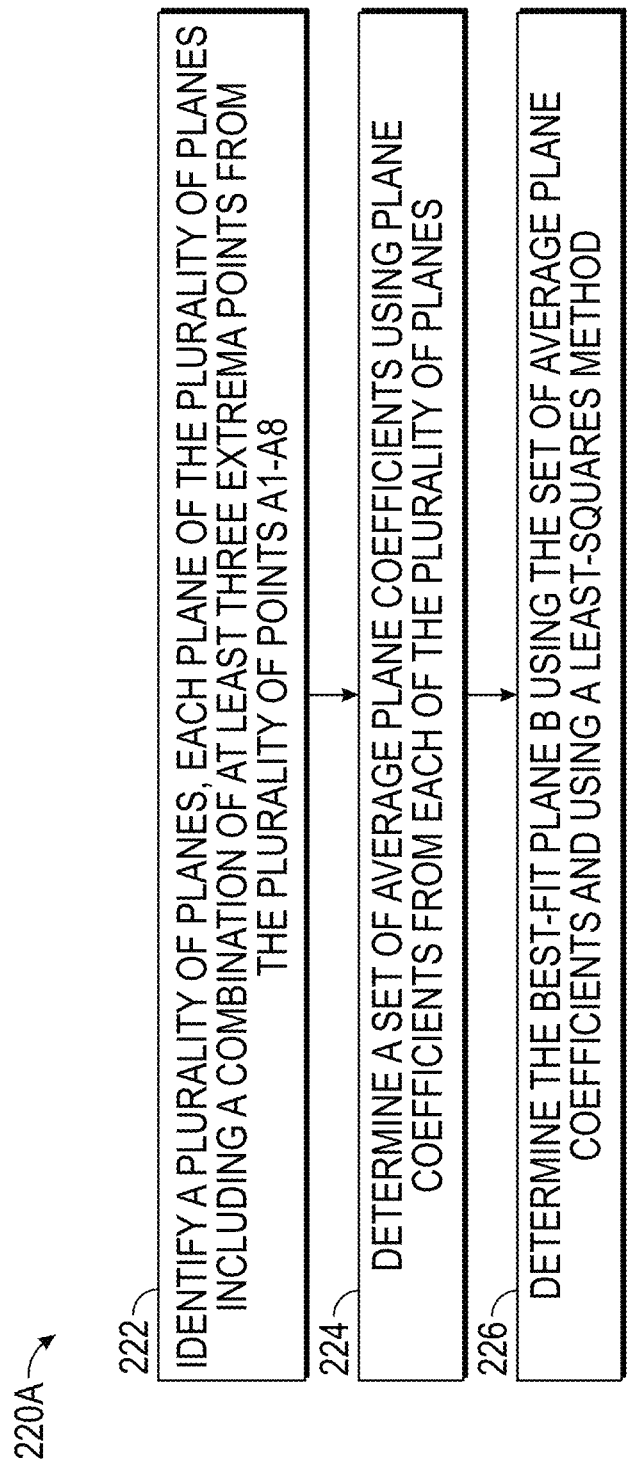

Step 220 of method 200 is shown in FIGS. 4 and 5 and illustrated in FIGS. 6 and 7. Two methods have been used to determine the best-fit plane B in step 220. The first method 220A is outlined in sub-steps 222, 224 and 226 of FIG. 5A in which the system 100 determines the best-fit plane B is using the plurality of extrema points A1-A8 using the least-squares methodology by identifying a plurality of planes and determining a set of average plane coefficients using plane coefficients from each of the plurality of planes. The best-fit plane B is considered a plane which results in a minimum sum of squares of respective perpendicular distances between each of the plurality of extrema points A1-A8 and the best-fit plane B. A second method 220B is outlined in FIG. 5B that considers the best-fit plane B to be a plane perpendicular to a line joining the structure of interest S and the centroid of the extrema points A1-A8, which results in a minimum sum of squares of respective perpendicular distances between each of the plurality of extrema points A1-A8 and the best-fit plane B.

In step 222 shown in FIG. 5A, using various combinations of 3 points from the plurality of data points A1-A8, the system 100 determines a plane for each respective combination that contains each of the 3 points used. Then, in step 224, the system 100 obtains average plane equation coefficients of all the determined planes. These average plane equation coefficients are then considered to be initial condition coefficients; the system 100 solves for the best-fit plane B for each extrema point A1-A8 of the plurality of extrema points A1-A8 using a least-squares methodology in step 226.

The general equation of a plane can be expressed as follows:

$$Ax+By+Cz+D=0$$

wherein A, B and C are the coefficients of the slope in the directions of the x, y and z axes respectively, and D is the coefficient representing the distance from the plane to the origin.

To calculate a plane from 3 points $P0=(x_0, y_0, z_0)$, $P1=(x_1, y_1, z_1)$ and $P2=(x_2, y_2, z_2)$, as in step 222, first calculate two vectors between the 3 points:

$$\text{Vector } P0-P1=(x_{v1},y_{v1},z_{v2})=(x_1-x_0,y_1-y_0,z_1-z_0)$$

$$\text{Vector } P0-P2=(x_{v2},y_{v2},z_{v2})=(x_2-x_0,y_2-y_0,z_2-z_0)$$

To calculate the A, B and C coefficients of the plane as in step 224, cross multiply the two vectors to get the normal vector of the plane, so:

$$A=y_{v1}z_{v2}-z_{v1}y_{v2}$$

$$B=z_{v1}x_{v2}-x_{v1}z_{v2}$$

$$C=x_{v1}y_{v2}-y_{v1}z_{v2}$$

Taking one of the points, the coefficient D can then be calculated from the plane equation:

$$D=-(Ax_0+By_0+Cz_0)$$

In some embodiments the plurality of extrema points A1-A8 include eight discrete points A1-A8, but in other embodiments can include more than or less than eight. For a plurality of extrema points A1-A8 equaling eight in number, 56 separate plane equations are determined from 56 combinations of 3 points from the set of 8 points A1-A8 in step 222 of method 200.

The coefficients of the average plane were calculated from the average of the A, B, C and D coefficients for the 56 planes according to step 224 shown in FIG. 5A:

$$A_{average} = \frac{A_1 + A_2 + \ldots + A_{56}}{56}$$

$$B_{average} = \frac{B_1 + B_2 + \ldots + B_{56}}{56}$$

$$C_{average} = \frac{C_1 + C_2 + \ldots + C_{56}}{56}$$

$$D_{average} = \frac{D_1 + D_2 + \ldots + D_{56}}{56}$$

Referring to step 226 of method 200 shown in FIG. 5A, for each extrema point A1-A8 of the plurality of extrema points A1-A8, a plurality of distances D1-D8 (FIG. 6) from the structure of interest S $(x_0, y_0, z_0)$ and the best-fit plane B $(Ax+By+Cz+D=0)$ are determined by the system 100 using the formula:

$$\text{distance} = \frac{|Ax_0 + By_0 + Cz_0 + D|}{\sqrt{A^2 + B^2 + C^2}}$$

The plurality of distances D1-D8 are then squared and added together. This quantity is used as an objective, and for this problem, the system 100 minimizes the quantity by varying the values of the A, B, C and D coefficients. Initial values of the coefficients A, B, C and D used by the system 100 are the coefficients of an average plane as determined in step 224.

In method 220B having associated sub-steps 223, 225 and 227 (FIG. 5B), the best-fit plane B is also determined using the plurality of extrema points A1-A8 using the least-squares methodology. The best-fit plane B is considered to be the plane perpendicular to the line joining the structure of interest S and the centroid of the extrema points A1-A8, which results in a minimum sum of squares of respective perpendicular distances between each of the plurality of extrema points A1-A8 and the best-fit plane B.

In step 223 shown in FIG. 5B, the centroid Ce of the plurality of data points A1-A8 is determined from the average of the data points.

$$\text{Centroid}(Ce) = \left( \frac{x_1 + x_2 + \ldots + x_8}{8}, \frac{y_1 + y_2 + \ldots + y_8}{8}, \frac{z_1 + z_2 + \ldots + z_8}{8} \right)$$

Where $x_n$ is the x coordinate, $y_n$ is the y coordinate and $z_n$ is the z coordinate of the $n^{th}$ data point.

In step 225 shown in FIG. 5B, the central axis of the cone CA of the cone is described as the line between the structure of interest S and the centroid of the plurality of data points Ce. It is calculated as the difference vector between the two points.

$$CA=Ce-S$$

The best-fit plane is described as a plane perpendicular to this central axis. From the parametric equation of a plane, the equation of a plane perpendicular to the central axis CA, can be described as:

$$x_{CA}x+y_{CA}y+z_{CA}z+D=0$$

Where $x_{CA}$, $y_{CA}$ and $z_{CA}$ are the x, y and z parameters respectively of the central axis CA.

Referring to step 227 of method 200 shown in FIG. 5B, for each of the plurality of extrema points A1-A8, a plurality of distances D1-D8 (FIG. 5B) from the structure of interest S $(x_0, y_0, z_0)$ and the best-fit plane B $x_{CA}x+y_{CA}y+z_{CA}z+D=0$ are determined using the formula:

$$\text{distance} = \frac{|Ax_0 + By_0 + Cz_0 + D|}{\sqrt{A^2 + B^2 + C^2}}$$

The plurality of distances D1-D8 are then squared and added together. This quantity is used as an objective, and for this problem, the system 100 minimizes the quantity by varying the value of the D coefficient. An initial value of the coefficient D used by the system 100 is calculated by setting the plane such that the plane intersects with the centroid Ce of the data points, and solving for D.

For either of the two versions of step 220, the system 100 checks that the result is correct by ensuring that the sum of the squares of the distances D1-D8 from each point A1-A8 to the least-squares best-fit plane B is lower than the sum of the squares of the distances between each point A1-A8 and the average plane determined in step 224. The least-squares best-fit plane B, shown in FIG. 7, is used as the plane for the base of the cone shape.

Referring to step 230 of method 200, the plurality of extrema points A1-A8 must be translated onto the best-fit plane B to generate 3-D translated points A1'-A8', as shown in FIGS. 8A-8B. To maintain the shape of the cone, the system 100 translates each extrema point A1-A8 of the plurality of extrema points A1-A8 onto the best-fit plane B along a line between each respective point A1-A8 and the structure of interest S. Step 230 ensures that the cross-section profile of the cone shape is unaltered when the plurality of extrema points A1-A8 are translated.

For each point A1-A8, a vector between each one of the plurality of extrema points A1-A8 $(x_0, y_0, z_0)$ and the structure of interest S $(x_s, y_s, z_s)$ is determined by the system 100 as follows:

$$V=(x_v,y_v,z_v)=(x_s-x_0, y_s-y_0, z_s-z_0)$$

A multiplication factor, t, representing a distance between the point A1-A8 and the best-fit plane B $Ax+By+Cz+D=0$ is determined as follows:

$$t = \frac{-(Ax_s + By_s + Cz_s + D)}{Ax_0 + By_0 + Cz_0}$$

The coordinates of each of the plurality of 3-D translated points A1'-A8' after translation onto the best-fit plane B are then determined by:

$$(x_{0\text{-}translated}, y_{0\text{-}translated}, z_{0\text{-}translated})=(tx_0, ty_0, tz_0)$$

The system 100 then performs two checks at this stage to verify that the translated points are on the best-fit plane. The first is an equality check of the plane equation $Ax+By+Cz+D=0$, and the second is a calculation of the distance between the point and the plane, which should be 0 (or near 0, allowing for calculation rounding).

Referring to steps 240 and 250, the system 100 determines an area on the best-fit plane B enclosed by 2-D translated points A1"-A8" using Gauss' shoelace formula. Gauss' shoelace formula calculates an enclosed area of an irregular polygon from 2-D coordinates of the vertices of the polygon. Calculating the area with this method requires mapping of the plurality of 3-D translated points A1'-A8' from a 3-D coordinate system to a 2-D coordinate system, as shown in step 240. As the 3-D translated points A1'-A8' are all on the best-fit plane B after translation, this is possible by creating a new 2-D coordinate system on the best-fit plane B.

The choice of origin is arbitrary, but to make any 2-D plot simpler, the system 100 takes a centroid of the plurality of 3-D translated extrema points A1'-A8' as the new origin in step 241. The centroid is determined according to step 242 by taking average x, y and z coordinates of each point of the plurality of 3-D translated extrema points A1'-A8'.

$$\text{Centroid } A =$$
$$(x_A, y_A, z_A) = \left(\frac{x_1 + x_2 + \ldots + x_8}{8}, \frac{y_1 + y_2 + \ldots + y_8}{8}, \frac{z_1 + z_2 + \ldots + z_8}{8}\right)$$

The axes of the new coordinate system must be perpendicular to each other. In step 243, two vectors are defined on the best-fit plane B using the centroid A and two of the translated points P1=$(x_1, y_1, z_1)$ and P2=$(x_2, y_2, z_2)$.

$$\text{Vector } V=(x_v,y_v,z_v)=P1-A$$

$$\text{Vector } U=(x_u,y_u,z_u)=P2-A$$

These vectors are then normalized (resized to have a length of 1):

$$|V| = \left(\frac{x_v}{\sqrt{x_v^2 + y_v^2 + z_v^2}}, \frac{y_v}{\sqrt{x_v^2 + y_v^2 + z_v^2}}, \frac{y_v}{\sqrt{x_v^2 + y_v^2 + z_v^2}}\right)$$

$$|U| = \left(\frac{x_u}{\sqrt{x_u^2 + y_u^2 + z_u^2}}, \frac{y_u}{\sqrt{x_u^2 + y_u^2 + z_u^2}}, \frac{y_u}{\sqrt{x_u^2 + y_u^2 + z_u^2}}\right)$$

The system 100 determines a vector, W, which is perpendicular to both |U| and |V| (and therefore perpendicular to the best-fit plane B), from the cross-product of |U| and |V| in step 244.

$$W=|V|\times|V|$$

A new U vector, which is perpendicular to |V| and W (and therefore on the best-fit plane B), but perpendicular to the vector |V|, is determined in step 245 from the cross-product of |V| and |W|:

$$U_{new}=|V|\times W$$

This new vector U is then normalized (resized to have a length of 1), using the same equation as before.

As the vectors $|U_{new}|=(x_u, y_u, z_u)$ and $|V|=(x_v, y_v, z_v)$ are perpendicular, they can be used as the axes for the 2D coordinate system on the best-fit plane. The system 100 converts each 3D translated point A1'-A8' $(x_0, y_0, z_0)$ to a 2D translated point A1"-A8" in a 2D coordinate system $(x_{0\text{-}2D}, y_{0\text{-}2D})$ in step 246 follows:

$$x_{0\text{-}2D}=x_u(x_0-x_A)+y_u(y_0-y_A)+z_u(z_0-z_A)$$

$$y_{0\text{-}2D}=x_v(x_0-x_A)+y_v(y_0-y_A)+z_v(z_0-z_A)$$

The system 100 then checks the mapping of the plurality of extrema points A1-A8 to the 2-D coordinate system in step 247 by calculating the distance between each adjacent pair of points in the 3-D coordinate system and in the 2-D coordinate system. If the mapping is done correctly, the distance between the points in the 3-D and 2-D coordinate systems should be the same.

Now that the plurality of extrema points A1-A8 are mapped to a 2-D coordinate system, the area of the shape enclosed by the points can be determined according to step 250 using the shoelace formula:

$$A = \frac{1}{2}\left(\left|\begin{matrix}x_1 & x_2 \\ y_1 & y_2\end{matrix}\right| + \left|\begin{matrix}x_2 & x_3 \\ y_2 & y_3\end{matrix}\right| + \ldots + \left|\begin{matrix}x_8 & x_1 \\ y_8 & y_1\end{matrix}\right|\right)$$

Where $$\left|\begin{matrix}x_1 & x_2 \\ y_1 & y_2\end{matrix}\right|$$

is the determinant of the matrix, given by:

$$\left|\begin{matrix}x_1 & x_2 \\ y_1 & y_2\end{matrix}\right| = x_1 y_2 - y_1 x_2$$

Referring to step 260 of method 200, the height of the cone shape C, h, is determined as the perpendicular distance between the best-fit plane B Ax+By+Cz+D=0 and the apex point S ($x_s$, $y_s$, $z_s$), as shown in FIG. 9:

$$h = \frac{|Ax_s + By_s + Cz_s + D|}{\sqrt{A^2 + B^2 + C^2}}$$

As shown in step 270 of method 200, the volume of surgical freedom can be calculated from the area (A) enclosed by the points on the best-fit plane (B) and the height of the cone shape (h):

$$\text{Volume} = \frac{1}{3} \times A \times h$$

In some embodiments of the method 200, to determine a volume of surgical freedom V' at a fixed distance from the structure of interest, the system 100 translates the best-fit plane B in 3-D space to a fixed perpendicular distance from the structure of interest S while maintaining a slope of the best-fit plane B between steps 220 (including sub-steps 222, 224 and 226) and 230 of method 200.

The volume calculation is dependent on the length of the probe 112 that is used to obtain the point data, as the length of the probe 112 will determine the height of the cone shape. If this factor is removed from the calculation, then the resulting values of volume of surgical freedom will be directly comparable to all other calculations using method 200, regardless of the length of the probe 112 being used to take the measurements.

In some embodiments, to remove the influence of the probe length from the volume determination, the system 100 can fix the height of the cone shape such that irrespective of the probe length, a normalized volume is calculated from the remaining volume of the cone when it is sliced at a fixed distance from the structure of interest S. The normalized height of the cone is somewhat arbitrary and was chosen as 10 mm in some embodiments, but other values may be selected as well. The reason for this is that the volume of surgical freedom value resulting from experimental data were in the range 5-20 mm³. This is a small enough number that it is easily comparable with other numbers of a similar size.

Normalization of the cone shape height is achieved by translating the best-fit plane B in 3-D space to a fixed perpendicular distance from the structure of interest S while maintaining a slope of the best-fit plane B between steps 220 and 230 of the method 200. After calculating the best-fit plane B using the method 200, the best-fit plane B is moved in 3-D space so that the perpendicular distance between the structure of interest S and a translated plane B' is at the required normalized cone height. As this is effectively moving the best-fit plane B to get a cross-section of the cone shape at a different distance from the structure of interest S, it is important that the slopes of the plane in the x, y and z directions (i.e. the A, B and C coefficients of the best-fit plane equation) remains constant, so that the translated plane B' is parallel to the best-fit plane B. Given this constraint, a relation for a perpendicular distance between the translated plane B' Ax+By+Cz+D'=0, and the structure of interest S ($x_s$, $y_s$, $z_s$) can be rearranged to give:

$$D' = h_{norm}(\sqrt{A^2+B^2+C^2}) - (Ax_s + By_s + Cz_s)$$

which can be substituted for D in step 230 of method 200. As the method for translating the points onto the best-fit plane moves each extrema point A1-A8 of the plurality of extrema points A1-A8 along the lines D1-D8 from their original locations, this step is equally applicable when calculating the normalized volume by translating the points to the normalized-height plane B' instead of the best-fit plane B, and using the normalized-plane B' instead of the best-fit plane B in all subsequent calculations, to find a normalized volume of surgical freedom.

In some embodiments, the computing system 300 is further operable to generate a 3-D visualization of the surgical corridor 10 using the measurements provided by the navigator 110 and the volume of surgical freedom as determined using the method 200. In some embodiments, the 3-D visualization may include a representation of the cone C as determined using the method 200 similar to FIGS. 3A and 3B. In some embodiments, the system 100 implements aspects of the method 200 using the computing system 300. Computing system 300 includes a memory 340 in communication with a processor 520 that stores and executes the system application 400 which is illustrated in FIGS. 10-22.

VSF Calculator System

Figure 21:
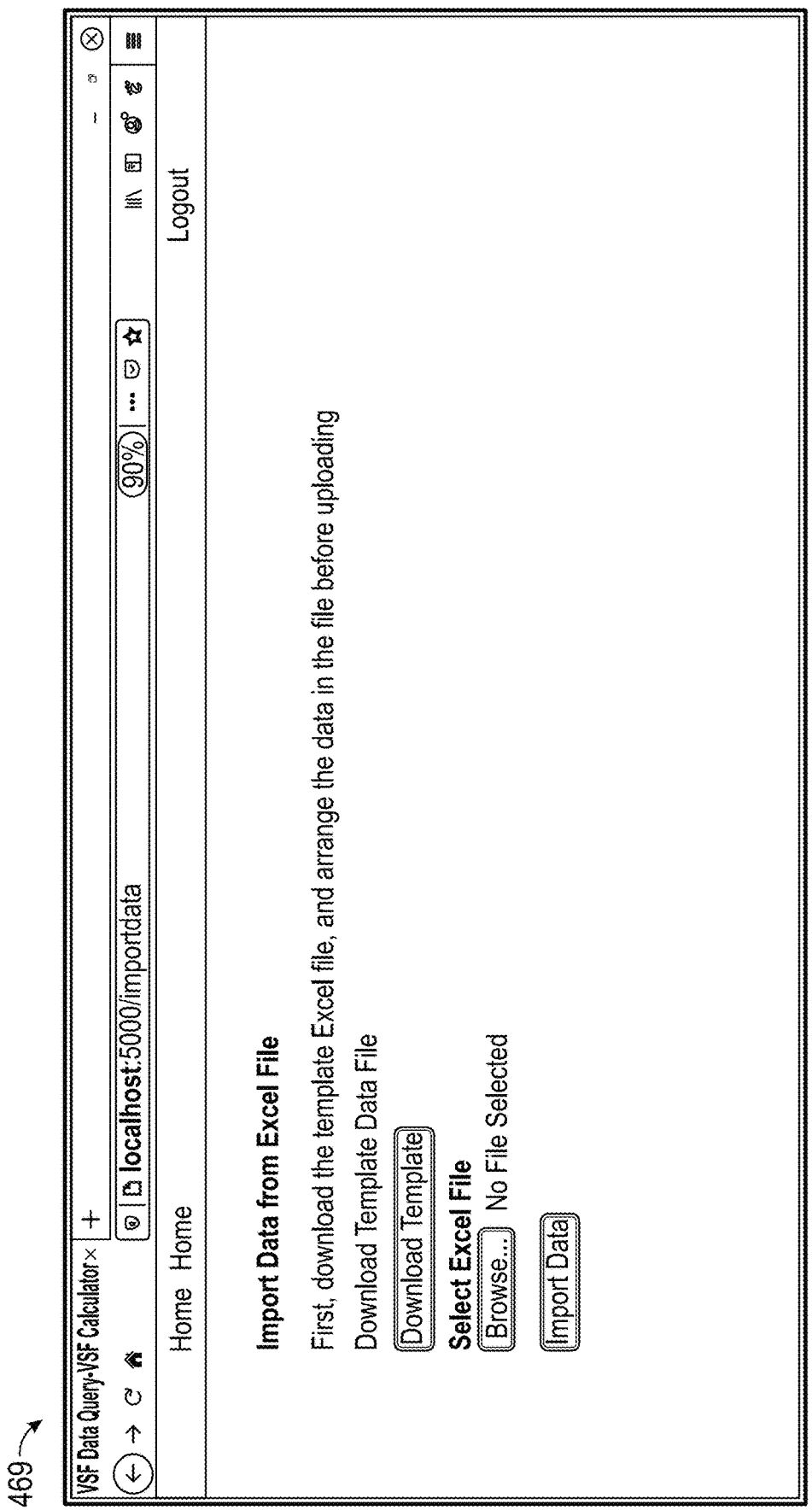
FIG. 21 is a screenshot showing a data import page of the system application of FIG. 10.
Figure 22:
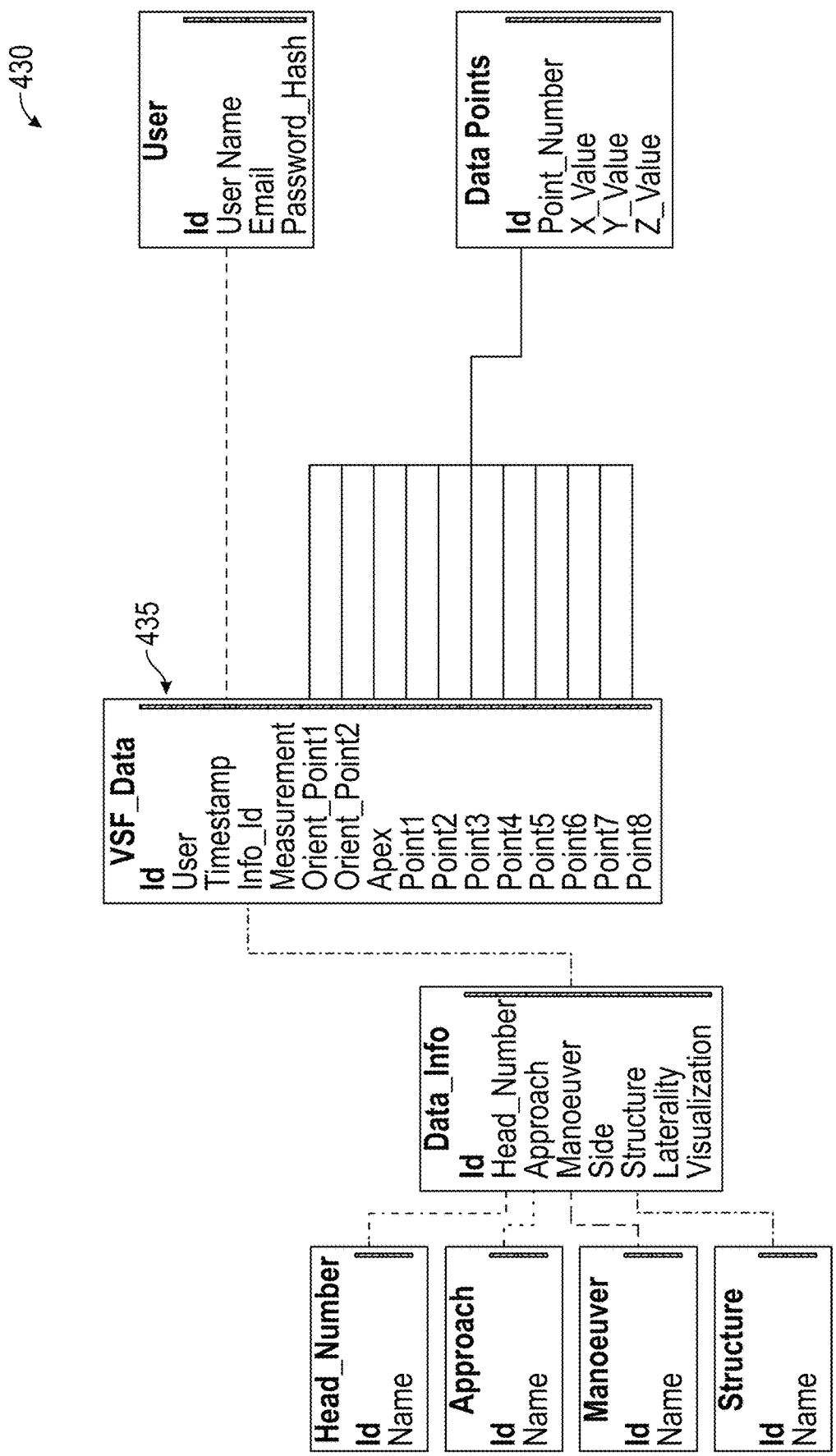
FIG. 22 is a diagram showing a database layout for the system application of FIG. 10.

Referring to FIGS. 10-22, in one embodiment of the system application 400 defines a plurality of modules 420 including a metric calculator module 422 for implementation of the method 200 for characterizing, assessing, and modeling a three-dimensional volumetric measurement of a surgical instrument's maneuverability within the surgical corridor with respect to access to a specific anatomic structure. The plurality of modules 420 communicate with a database 430 that includes the anatomical coordinate data of the structure of interest S and the plurality of extrema points A1-A8 within the body for calculation of the volume of surgical freedom and related metrics according to method 200. In some embodiments, the database 430 receives and stores three-dimensional positional data from the navigation system 110 of the system 100 for a plurality of specimens. Each specimen corresponds to at least one dataset 435 (FIG. 22). In some embodiments, each dataset 435 includes three-dimensional positional coordinate data taken using the probe 112 for various reference points including the structure of interest S and the plurality of extrema points A1-A8. In one embodiment shown in FIGS. 11A and 11B, one embodiment of a user interface 440 of the system application 400 is shown. In one embodiment of the system 100, the 3-D coordinates of the structure of interest S and the plurality of extrema points A1-A8 are taken using the navigation system 110 (FIG. 1). FIGS. 11A and 11B in particular illustrate a simplified embodiment of an excel-based implementation of the system application 400.

Figure 12:
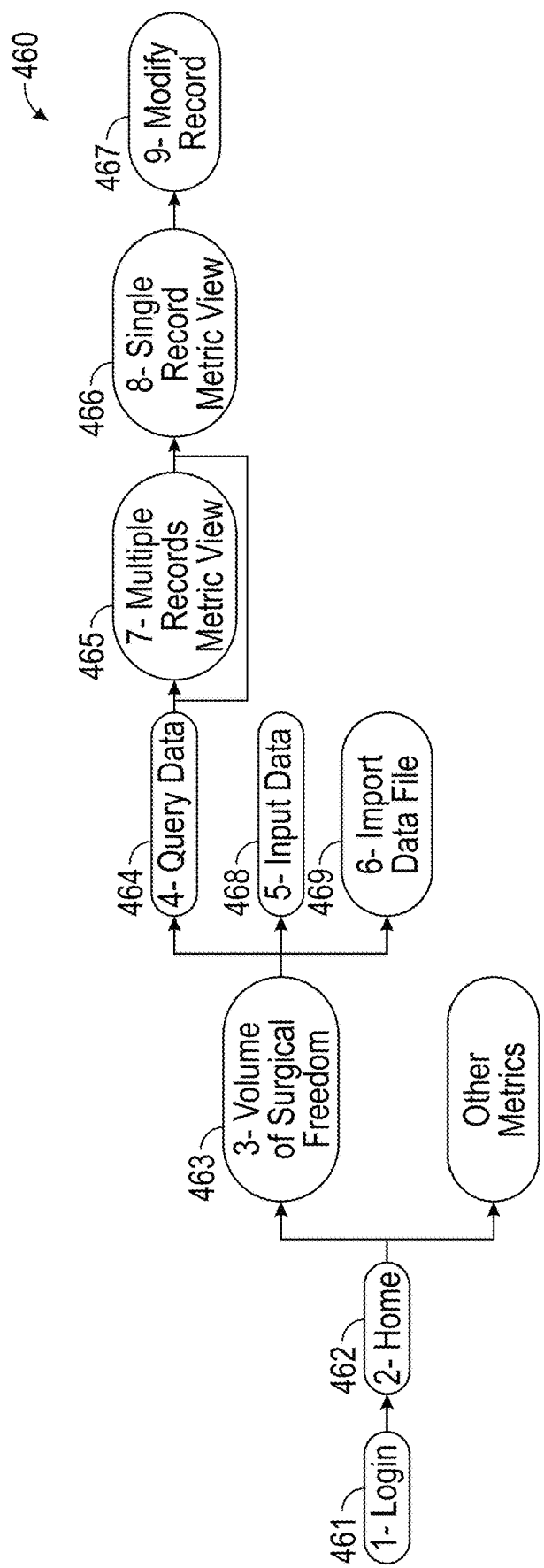
FIG. 12 is a diagram showing a navigation layout for a user interface (UI) of the system application of FIG. 10.
Figure 14:
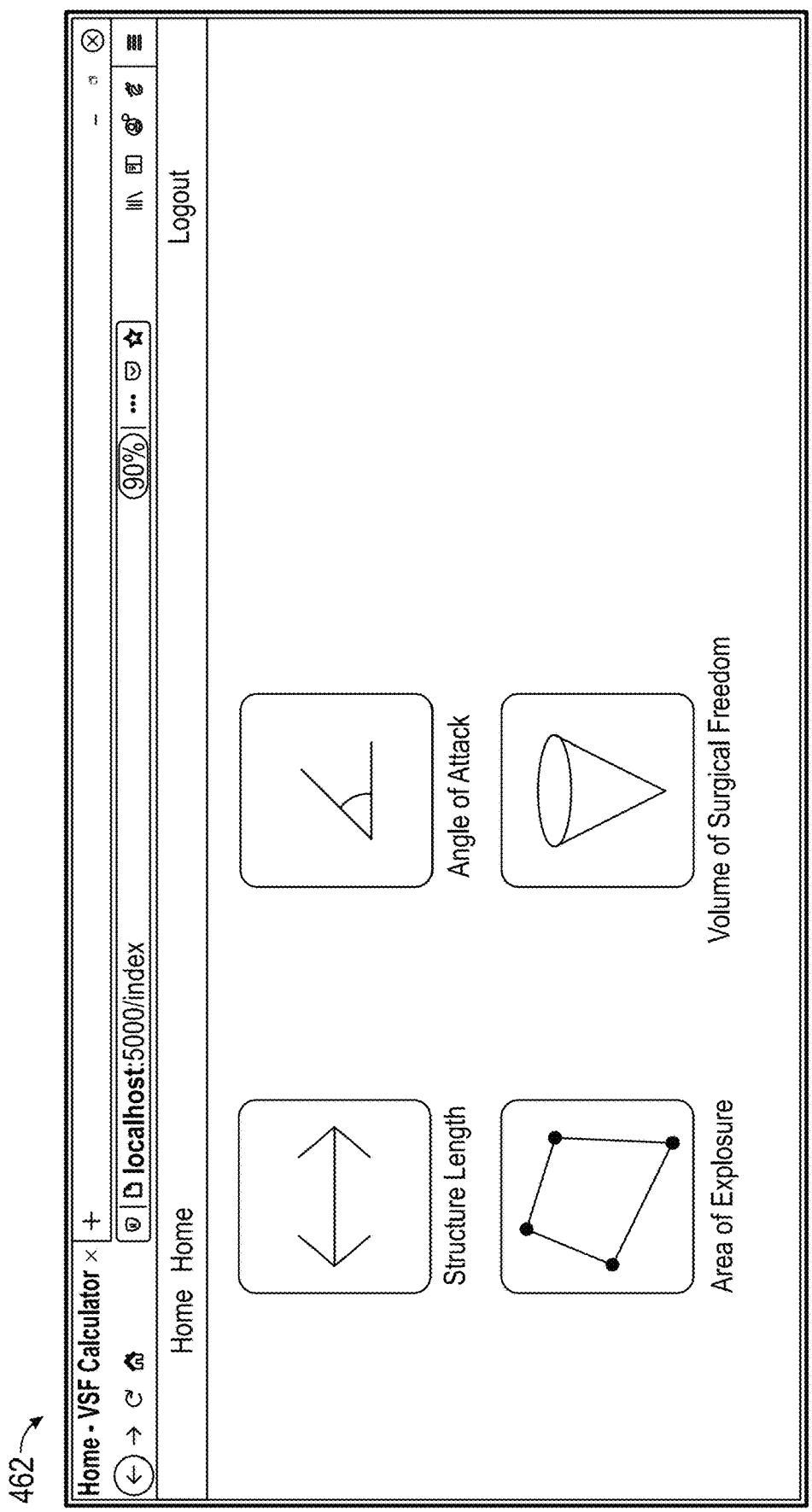
FIG. 14 is a screenshot showing an index page of the system application of FIG. 10.
Figure 15:
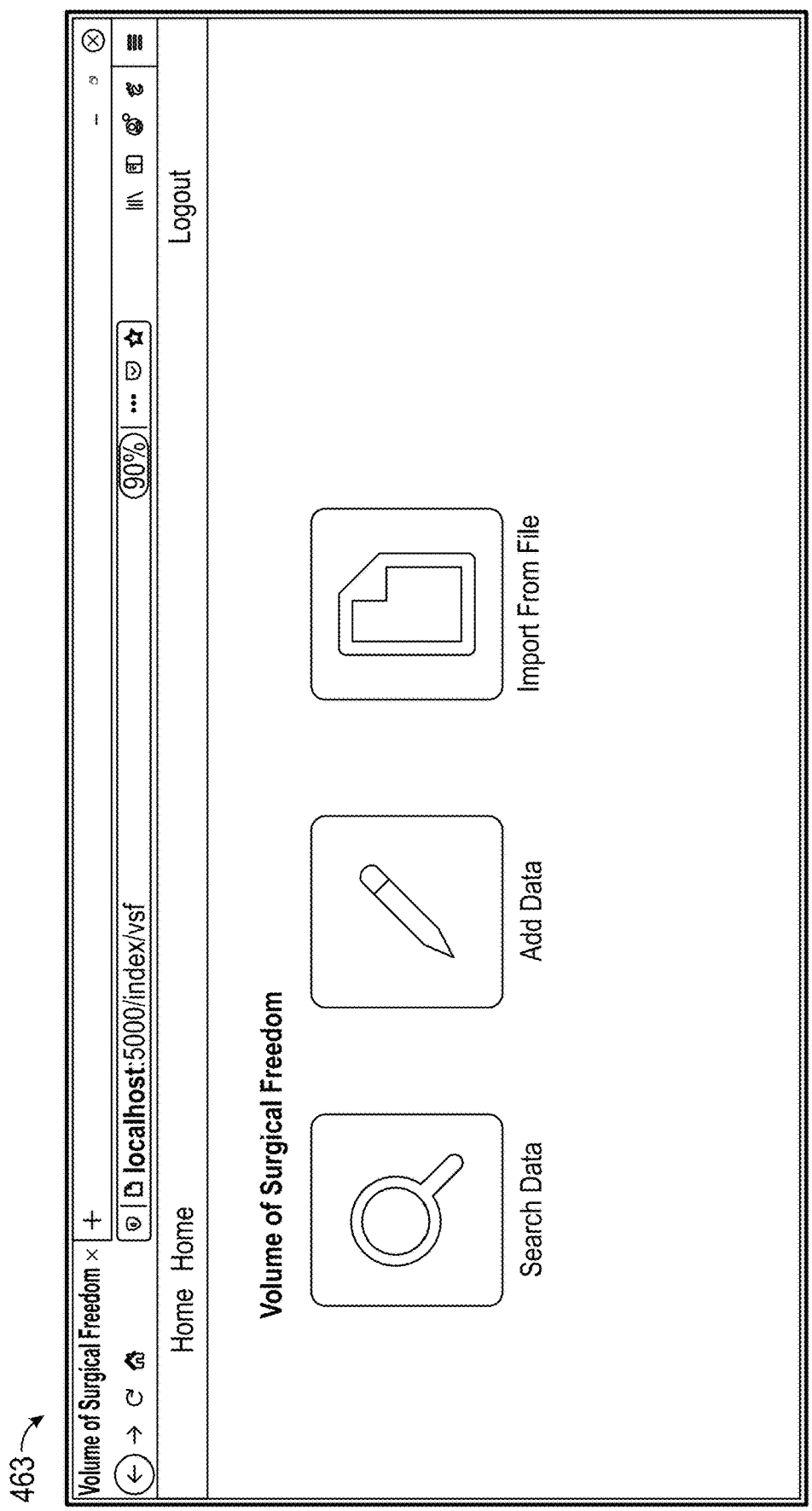
FIG. 15 is a screenshot showing an overview page for all data operations relating to the volume of surgical freedom (VSF) metric of the system application of FIG. 10.

As shown in the embodiments of FIGS. 12-22, the system application 400 can be accessed through a web browser 450. An application navigation showing a plurality of pages 460 of the system application 400 is provided in FIG. 12. As shown, the system application 400 includes a login page 461. A user that is not logged in is redirected to this page when trying to access any of the application content. Once the user is logged in, they have access to the application content. As illustrated in FIGS. 12 and 14, the system application 400 includes an index page 462. In some embodiments, the index page 462 is the base page of the application navigation tree illustrated in FIG. 12 and provides access to all application content. Once a user is successfully logged in, they are redirected to this index page 462. The index page 462 includes links to the different parts of the system application 400. In some embodiments of the system application 400, the index page 462 includes four images that include links to the four metrics supported by the calculator; one of the four metrics being a Volume of Surgical Freedom as discussed herein. Referring to FIGS. 12 and 22, the system application 400 includes an overview page 463 for all data operations relating to the volume of surgical freedom metric. In some embodiments, data operations which are linked from this page can include:

Search Data (query data page 464 (FIG. 16))
Add Data
Import Data from File

Figure 17:
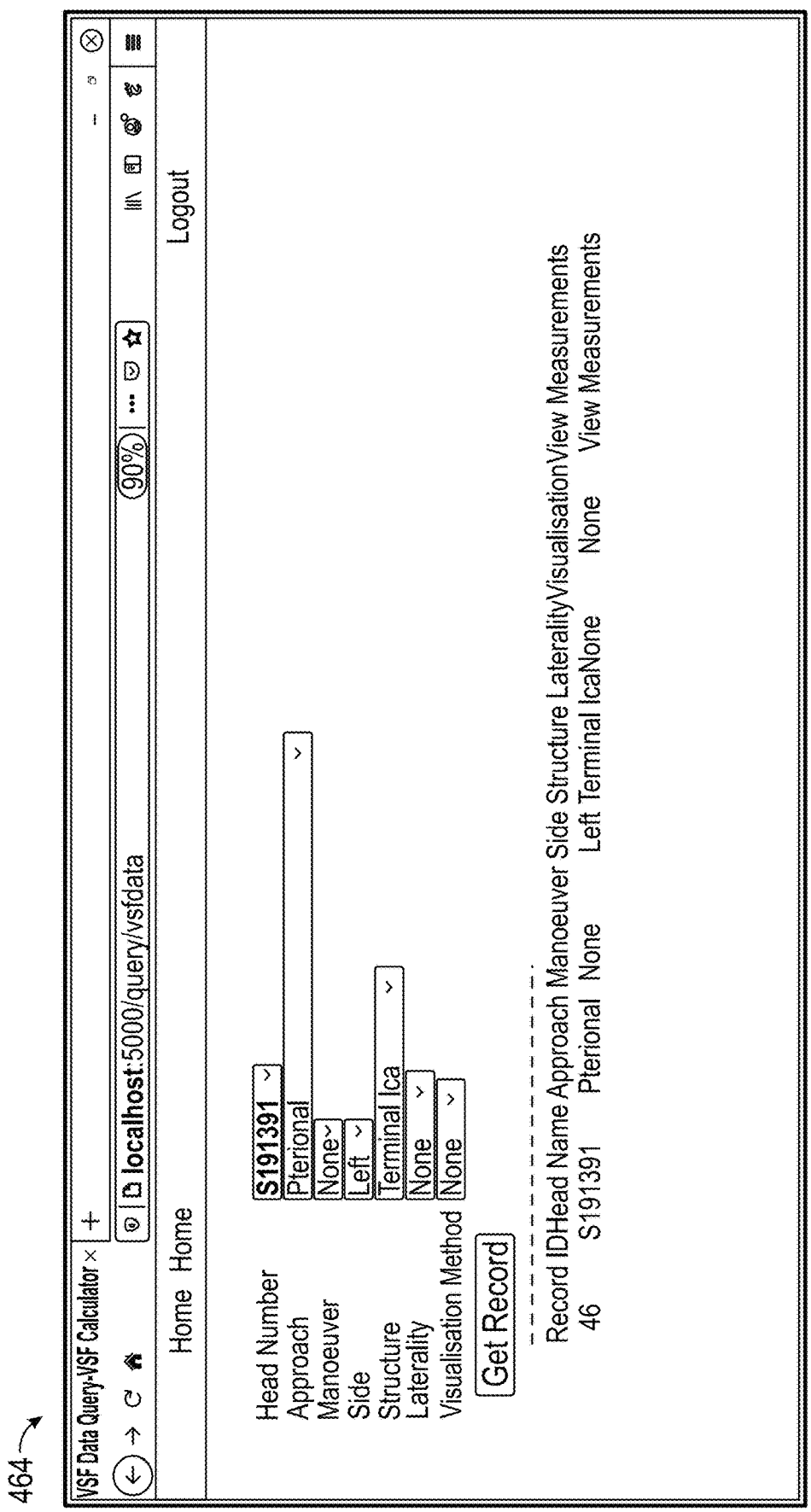
FIG. 17 is a screenshot showing results of the search page of FIG. 16.

As further shown in FIGS. 12, 16 and 17, the system application 400 includes a query data page 464, which is used to search for individual measurements for calculating metrics, and to view the raw data for individual records. The drop-down menus are populated with all the relevant fields which are stored in the database, and each information field can be selected for the query. The dataset information is used to search records in the database. On executing a search, the search results are displayed on the page, as in FIG. 17. The metric view for the data can be accessed from the "View Measurements" link.

Figure 18:
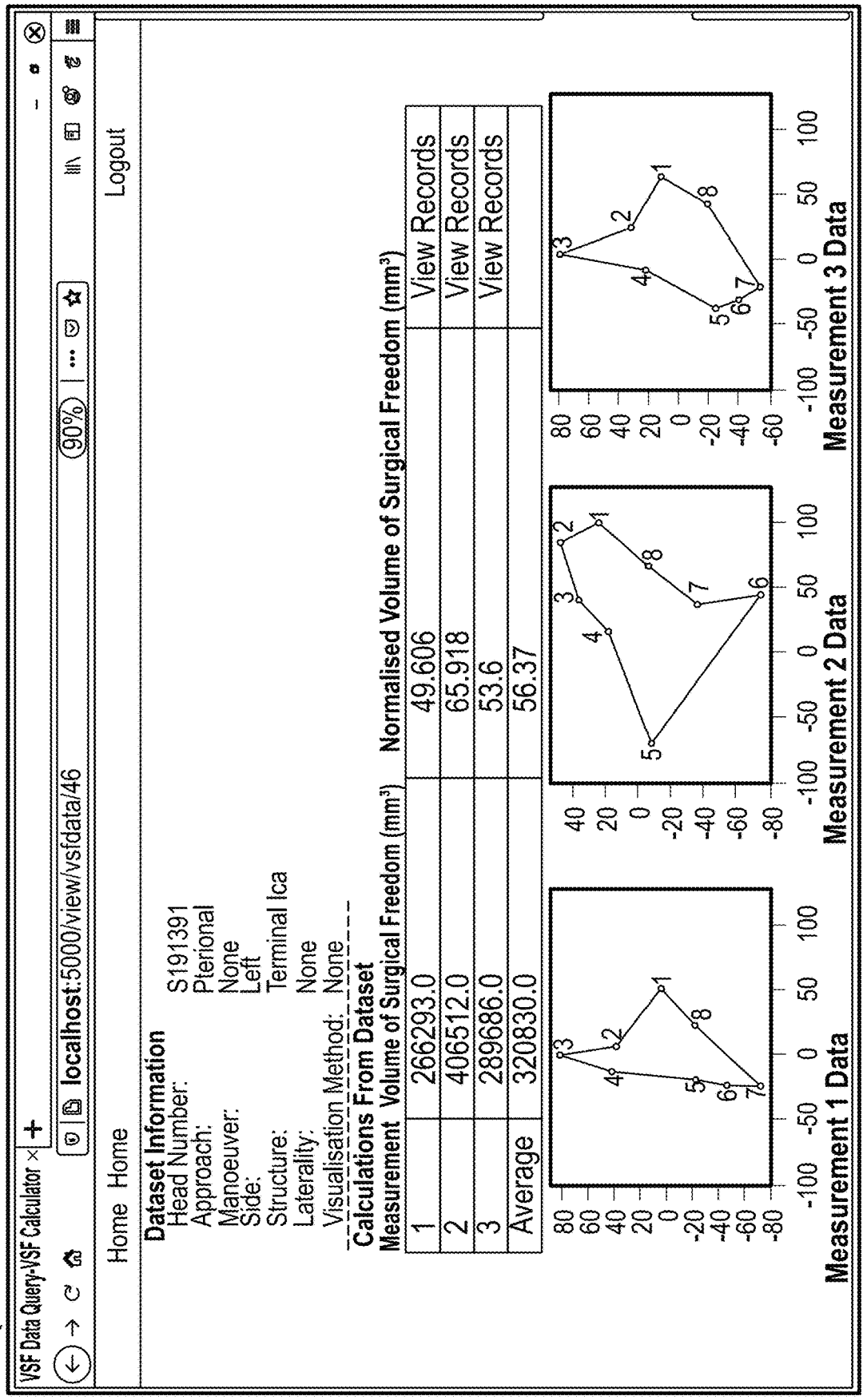
FIG. 18 is a screenshot showing a metric view of the results of FIG. 17.

As illustrated in FIGS. 12 and 18, the system application 400 includes a metric view 465 of multiple datasets 435 of data, which displays dataset information specific to the record, the calculated metric for each record and 2-D images of the data. For each dataset information, there can exist more than one measurement, due to repeated measurements for data verification. The metric view page 465 displays all the measurements that are stored in the database associated with the dataset information for a particular dataset 435, including the determination of the volume of surgical freedom obtained in step 270 of method 200 and related measurements. In some embodiments, the metric view page 465 can also include a three-dimensional rendering of the surgical corridor such as the rendering in FIG. 9. If there are more than one measurement associated with the dataset information, an average value of the metrics for all measurements is displayed in addition to the individual metrics for each measurement. The raw data for a single measurement can be viewed using the "View Record" link in the "Calculations from Dataset" table. In some embodiments, this link is only visible if the current logged-in user is the user who has entered this measurement data into the database. This is to protect data from indiscriminate editing. Only the user who has entered the data can view and edit the raw data.

Figure 19:
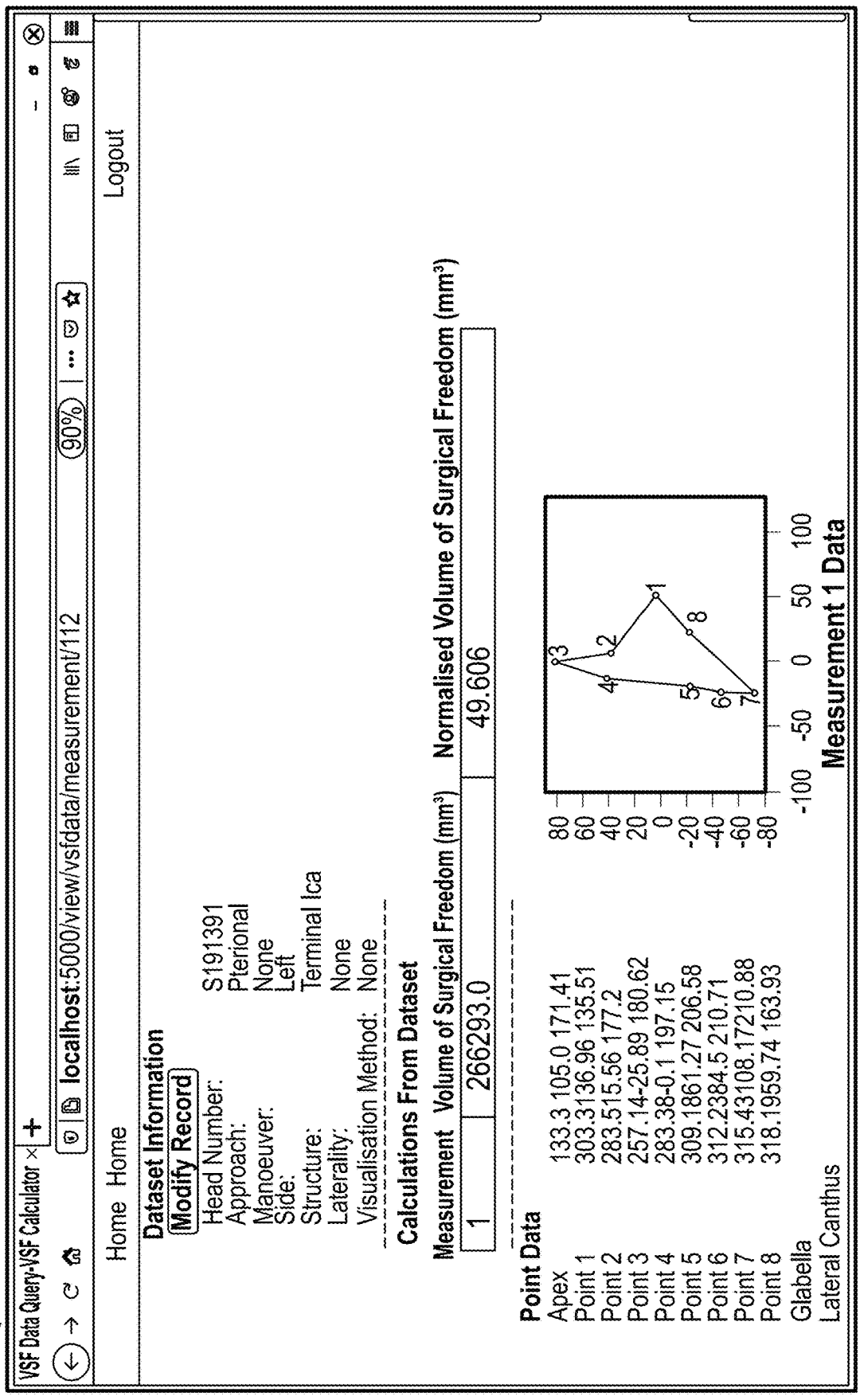
FIG. 19 is a screenshot showing a single record view page of the results of FIG. 16.

Further, as shown in FIGS. 12 and 19, the system application 400 includes a single record view page 466. This page displays the dataset information, the calculated metric, the raw data and a 2-D representation of the data for a single measurement. This page is only accessible to the user if that user input the record into the database. The raw data can be modified using the "Modify Record" button. As illustrated in FIGS. 12 and 20, the system application 400 includes a data modification page 467 This page shows the raw data of the record, in text input fields, so that any of the record coordinate points, or the data information relating to the record can be changed. Any changes can be saved to the database with the "Save Data" button. As shown in FIGS. 12, the system application 400 includes a data entry page 468. In some embodiments, the data entry page 468 is the same page as that used for modifying data, but no data is pre-entered. The user must enter the data information and the coordinate points for the measurement record. After the data is entered into the form, the user can display a graphical representation of the data using the "Plot Data" button. When the user selects the "Save Data" button, a check of all data fields is carried out to detect missing information, and the input data is validated before saving to the database. If any form fields are empty, or if any validation fails, the user is prompted with an error message. Referring to FIGS. 12 and 21, the system application 400 includes an import data file page 469 for importing data from a file. This allows the user to upload many measurement records quickly. In some embodiments, a standard file format is used to upload the data, so an empty file with the correct format can be downloaded from this page to be filled.

Database Model

Referring to FIG. 22, an example database architecture diagram 430 is illustrated for organizing data within the plurality of datasets 435 for operation of the system 100. For a particular embodiment, each dataset 435 in the database 430 requires the following information:
Surgical target structure
Surgical Approach
Head Side
Unique identifier for head (head number)
In addition, the following data should also be used to distinguish between different datasets 435:
Maneuver(s) used during approach
Laterality
Visualization method (endoscope or microscope)

Computer-Implemented System

Figure 23:
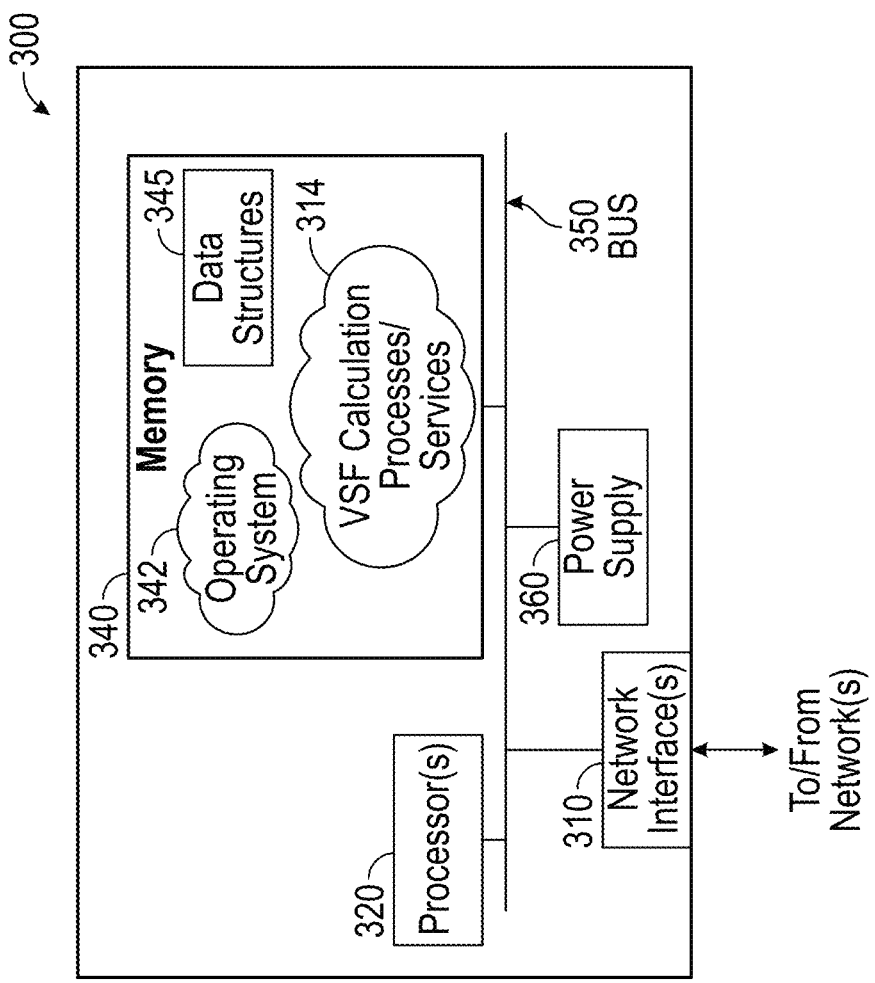
FIG. 23 is an exemplary computing system for use with the system of FIG. 1.

FIG. 23 is a schematic block diagram of an example device 300 that may be used with one or more embodiments described herein, e.g., as a component of system 100 and/or as computing system 300 shown in FIG. 1.

Device 300 comprises one or more network interfaces 310 (e.g., wired, wireless, PLC, etc.), at least one processor 320, and a memory 340 interconnected by a system bus 350, as well as a power supply 360 (e.g., battery, plug-in, etc.).

Network interface(s) 310 include the mechanical, electrical, and signaling circuitry for communicating data over the communication links coupled to a communication network. Network interfaces 310 are configured to transmit and/or receive data using a variety of different communication protocols. As illustrated, the box representing network interfaces 310 is shown for simplicity, and it is appreciated that such interfaces may represent different types of network connections such as wireless and wired (physical) connections. Network interfaces 310 are shown separately from power supply 360, however it is appreciated that the interfaces that support PLC protocols may communicate through power supply 360 and/or may be an integral component coupled to power supply 360.

Memory 340 includes a plurality of storage locations that are addressable by processor 320 and network interfaces 310 for storing software programs and data structures associated with the embodiments described herein. In some embodiments, device 300 may have limited memory or no memory (e.g., no memory for storage other than for programs/processes operating on the device and associated caches).

Processor 320 comprises hardware elements or logic adapted to execute the software programs (e.g., instructions) and manipulate data structures 345. An operating system 342, portions of which are typically resident in memory 340 and executed by the processor, functionally organizes device 300 by, inter alia, invoking operations in support of software processes and/or services executing on the device. These software processes and/or services may include VSF Calculation Processes/Services 314 which can in some embodiments include aspects of system application 400. Note that while VSF Calculation Processes/Services 314 is illustrated in centralized memory 440, alternative embodiments provide for the process to be operated within the network interfaces 410, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the VSF Calculation Processes/Services 314 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:
a processor in communication with a memory, the memory including instructions executable by the processor to:
convert a plurality of three-dimensional coordinates representative of locations of a plurality of extrema points of a surgical corridor to a two-dimensional coordinate system on a best-fit plane to obtain a plurality of two-dimensional translated extrema points;
determine an area of an irregular polygon enclosed by the plurality of two-dimensional translated extrema points;
determine a height from a location of a structure of interest within the surgical corridor to the best-fit plane; and
determine a volume of surgical freedom within the surgical corridor using the area of the irregular polygon and the height.

2. The system of claim 1, further comprising:
a probe in communication with a navigation system, wherein the probe and the navigation system are collectively operable to output, for an extrema point of the plurality of extrema points or for the structure of interest, a set of three-dimensional coordinates of the plurality of three-dimensional coordinates, the set of three-dimensional coordinates being representative of a location of the extrema point or the structure of interest.

3. The system of claim 2, wherein the set of three-dimensional coordinates is determined at a point-of-contact of the probe with the extrema point or the structure of interest.

4. The system of claim 1, wherein the memory further includes instructions executable by the processor to:
determine the best-fit plane in a three-dimensional space using the plurality of three-dimensional coordinates associated with each respective extrema point of the plurality of extrema points.

5. The system of claim 4, wherein the memory further includes instructions executable by the processor to:
identify a plurality of planes, wherein each plane of the plurality of planes includes a combination of at least three extrema points of the plurality of extrema points;
determine a set of average plane coefficients using a set of plane coefficients from each plane of the plurality of planes; and
determine the best-fit plane using a least-squares method and the set of average plane coefficients.

6. The system of claim 4, wherein the memory further includes instructions executable by the processor to:
determine a centroid of the plurality of extrema points;
determine a central axis, wherein the central axis is a line joining the structure of interest and the centroid; and
determine the best-fit plane perpendicular to the central axis using a least-squares method.

7. The system of claim 1, wherein the memory further includes instructions executable by the processor to:
translate each extrema point of the plurality of extrema points onto the best-fit plane to obtain a plurality of three-dimensional translated extrema points; and
convert the plurality of three-dimensional translated extrema points to the two-dimensional coordinate system on the best-fit plane to obtain the plurality of two-dimensional translated extrema points.

8. The system of claim 1, wherein each three-dimensional translated extrema point is associated with a set of three-dimensional translated coordinates.

9. The system of claim 1, wherein the memory further includes instructions executable by the processor to:
translate the best-fit plane to a selected perpendicular distance from the structure of interest along a central axis, wherein the central axis is a line joining the structure of interest and a centroid of the plurality of extrema points.

10. The system of claim 1, wherein the memory further includes instructions executable by the processor to:

display, by a display in communication with the processor, one or more metrics related to the volume of surgical freedom.

11. The system of claim 1, wherein the memory further includes instructions executable by the processor to:
display, by a display in communication with the processor, a three-dimensional rendering of the surgical corridor using the plurality of three-dimensional coordinates associated with the plurality of extrema points and the structure of interest.

12. A method, comprising:
converting, by a processor in communication with a memory, a plurality of three-dimensional coordinates representative of locations of a plurality of extrema points of a surgical corridor to a two-dimensional coordinate system on a best-fit plane to obtain a plurality of two-dimensional translated extrema points;
determining an area of an irregular polygon enclosed by the plurality of two-dimensional translated extrema points;
determining a height from a location of a structure of interest within the surgical corridor to the best-fit plane; and
determining a volume of surgical freedom within the surgical corridor using the area of the irregular polygon and the height.

13. The method of claim 12, further comprising:
capturing, by a probe in communication with a navigation system and the processor and for an extrema point of the plurality of extrema points or for the structure of interest, a set of three-dimensional coordinates of the plurality of three-dimensional coordinates, the set of three-dimensional coordinates being representative of a location of the extrema point or the structure of interest.

14. The method of claim 13, the set of three-dimensional coordinates being captured using the navigation system by measuring a location of a point-of-contact of the probe with the extrema point or the structure of interest.

15. The method of claim 12, further comprising:
determining the best-fit plane in a three-dimensional space using the plurality of three-dimensional coordinates associated with each respective extrema point of the plurality of extrema points.

16. The method of claim 15, further comprising:
identifying a plurality of planes, wherein each plane of the plurality of planes includes a combination of at least three extrema points from the plurality of extrema points;
determining a set of average plane coefficients using a set of plane coefficients from each plane of the plurality of planes; and
determining the best-fit plane using a least-squares method and the set of average plane coefficients.

17. The method of claim 15, further comprising:
determining a centroid of the plurality of extrema points;
determining a central axis, wherein the central axis is a line joining the structure of interest and the centroid; and
determining the best-fit plane perpendicular to the central axis using a least-squares method.

18. The method of claim 12, further comprising:
translating each extrema point of the plurality of extrema points onto the best-fit plane to obtain a plurality of three-dimensional translated extrema points; and
converting the plurality of three-dimensional translated extrema points to the two-dimensional coordinate system on the best-fit plane to obtain the plurality of two-dimensional translated extrema points.

19. The method of claim 12, further comprising:
translating the best-fit plane to a selected perpendicular distance from the structure of interest along a central axis, wherein the central axis is a line joining the structure of interest and a centroid of the plurality of extrema points.

20. The method of claim 12, further comprising:
displaying, by a display in communication with the processor, a three-dimensional rendering of the surgical corridor using the plurality of three-dimensional coordinates associated with the plurality of extrema points and the structure of interest.

* * * * *